United States Patent
Levner et al.

(10) Patent No.: US 10,335,788 B2
(45) Date of Patent: Jul. 2, 2019

(54) REMOVING BUBBLES IN A MICROFLUIDIC DEVICE

(71) Applicant: EMULATE, Inc., Boston, MA (US)

(72) Inventors: Daniel Levner, Brookline, MA (US); Josiah Daniel Sliz, Boston, MA (US); Christopher David Hinojosa, Cambridge, MA (US); Joshua Gomes, Somerville, MA (US); Kyung Jin Jang, Andover, MA (US)

(73) Assignee: Emulate, Inc., Boston, MA (US)

( * ) Notice: Subject to any disclaimer, the term of this patent is extended or adjusted under 35 U.S.C. 154(b) by 112 days.

(21) Appl. No.: 15/647,800

(22) Filed: Jul. 12, 2017

(65) Prior Publication Data

US 2018/0016536 A1     Jan. 18, 2018

Related U.S. Application Data

(60) Provisional application No. 62/361,266, filed on Jul. 12, 2016.

(51) Int. Cl.
*G01N 1/22* (2006.01)
*G01N 1/00* (2006.01)
(Continued)

(52) U.S. Cl.
CPC ... *B01L 3/502723* (2013.01); *B01L 3/502715* (2013.01); *B01L 3/502746* (2013.01); *B01L 3/502761* (2013.01); *C12M 21/08* (2013.01); *C12M 23/16* (2013.01); *C12M 23/40* (2013.01); *C12M 25/02* (2013.01); *C12M 29/10* (2013.01); *C12M 29/20* (2013.01); *B01L 2200/025* (2013.01); *B01L 2200/027* (2013.01); *B01L 2200/0605* (2013.01); *B01L 2200/0684* (2013.01); *B01L 2300/0681* (2013.01); *B01L 2300/0816* (2013.01); *B01L 2300/0887* (2013.01); *B01L 2300/10* (2013.01);
(Continued)

(58) Field of Classification Search
CPC ............. G01N 1/22; G01N 1/00; B01L 3/00
USPC .... 422/502, 503, 504; 436/43, 63, 174, 180, 436/181
See application file for complete search history.

(56) References Cited

U.S. PATENT DOCUMENTS

| 6,843,281 B1 * | 1/2005 | Barth ............... B01D 19/00 137/803 |
| 8,647,861 B2 | 2/2014 | Ingber et al. ............. 435/289.1 |

(Continued)

FOREIGN PATENT DOCUMENTS

| CN | 104225964 A | 9/2014 |
| EP | 2985063 A1 | 2/2016 |

(Continued)

OTHER PUBLICATIONS

Great Britain Office Action for the Great Britain Patent Application No. GB1711211.1 dated Dec. 23, 2017.
(Continued)

*Primary Examiner* — Brian J. Sines
(74) *Attorney, Agent, or Firm* — Medlen & Carroll, LLP

(57) ABSTRACT

Methods of removing bubbles from a microfluidic device are described where the flow is not stopped. Methods are described that combine pressure and flow to remove bubbles from a microfluidic device. Bubbles can be removed even where the device is made of a polymer that is largely gas impermeable.

26 Claims, 21 Drawing Sheets

(51) Int. Cl.
*B01L 3/00* (2006.01)
*C12M 3/06* (2006.01)
*C12M 1/00* (2006.01)
*C12M 3/00* (2006.01)
*C12M 1/12* (2006.01)

(52) U.S. Cl.
CPC ....... *B01L 2300/12* (2013.01); *B01L 2300/14* (2013.01); *B01L 2400/0487* (2013.01)

(56) References Cited

U.S. PATENT DOCUMENTS

| | | | |
|---|---|---|---|
| 9,011,797 B2 | 4/2015 | Gilbert et al. | 422/504 |
| 2002/0127740 A1* | 9/2002 | Ho | C12Q 1/6837 436/518 |
| 2004/0132218 A1* | 7/2004 | Ho | B01L 3/5025 436/524 |
| 2006/0263873 A1 | 11/2006 | Levine et al. | 435/288.5 |
| 2007/0068573 A1* | 3/2007 | Cox | G01N 27/44769 137/1 |
| 2007/0267335 A1 | 11/2007 | Gao et al. | 436/43 |
| 2008/0185057 A1 | 8/2008 | Prakash et al. | 137/806 |
| 2009/0126568 A1 | 5/2009 | Karaki et al. | 436/180 |
| 2009/0162864 A1 | 6/2009 | Kitazawa et al. | 435/6 |
| 2012/0088263 A1 | 4/2012 | Bruno et al. | 422/407 |
| 2012/0245042 A1 | 9/2012 | Liu et al. | 422/502 |
| 2014/0171343 A1* | 6/2014 | Su | G01N 21/05 506/39 |
| 2015/0251181 A1 | 9/2015 | Saito | 422/502 |
| 2016/0361715 A1* | 12/2016 | Shi | A61B 5/150022 |
| 2017/0058243 A1 | 3/2017 | Levner et al. | 422/502 |
| 2017/0058248 A1 | 3/2017 | Hinojosa et al. | 435/325 |
| 2018/0016537 A1* | 1/2018 | Levner | B01L 3/502715 |

FOREIGN PATENT DOCUMENTS

| | | |
|---|---|---|
| JP | 2006242607 A | 9/2006 |
| WO | WO/2010/092845 | 8/1910 |
| WO | WO/2012/064172 | 5/1912 |
| WO | WO/2014-039514 | 3/1914 |

OTHER PUBLICATIONS

PCT International Search Report of International Application No. PCT/US2017/041656 dated Sep. 21, 2017.

Kang, J. H. et al. (2008) "Analysis of pressure-driven air bubble elimination in a microfluidic device," *Lab on a Chip* 8(1), 176-178.

* cited by examiner

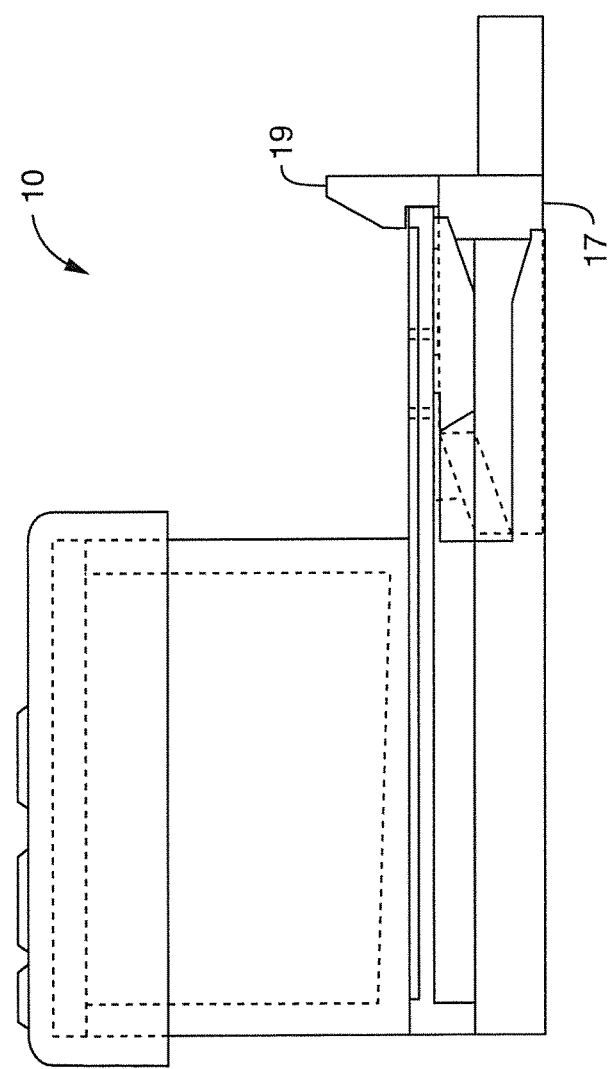

If $P_2 = 0$ ⟶ $r = \dfrac{P_1}{R}$

If $P_2 \neq 0$ ⟶ $r = \dfrac{(P_1 - P_2)}{R} = \dfrac{\Delta P}{R}$

| # OF CHIPS | MEDIUM VOLUMES | EQUILIBRATION REQUIREMENTS | TOTAL NUMBER OF MEDIA REFRESHES | EQUILIBRATION REQUIREMENTS | # OF PUMPS NEEDED |
|---|---|---|---|---|---|
| 72 | 250 mL APICAL + 250mL BASAL | 1 HR WATER BATH | 6 | 1 HR WATER BATH | 4 |
| | | 15 MIN DEGASSING (x3 - 50µL with 4 pumps) | | 15 MIN DEGASSING (x3 - 50µL with 4 pumps) | |
| | | 30 MIN INCUBATION AT 37°C $CO_2$ | | 30 MIN INCUBATION AT 37°C $CO_2$ | |

FIG. 10

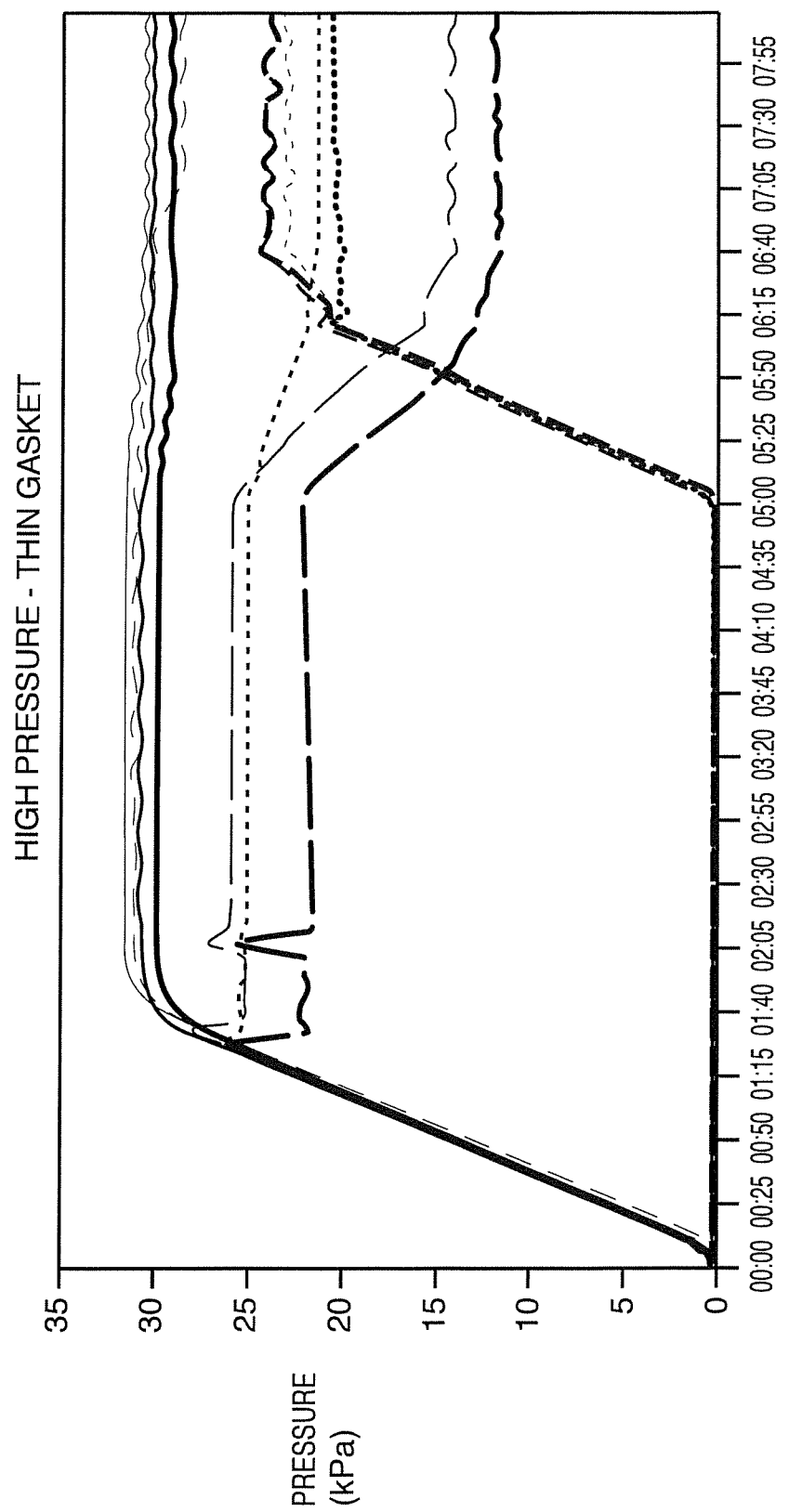

REMOVING BUBBLES IN A MICROFLUIDIC DEVICE

FIELD OF THE INVENTION

Methods of removing bubbles from a microfluidic device are described where the flow is not stopped. Indeed, methods are described that combine pressure and flow to remove bubbles from a microfluidic device. Bubbles can be removed even where the device is made of a polymer that is largely gas impermeable.

BACKGROUND

Bubbles inadvertently introduced into a microfluidic system can significantly and negatively affect device operation. It is nearly impossible to operate and fill these devices under bubble-free conditions. This is especially true for microfluidic perfusion culture systems, which typically require sterilization and pre-conditioning of the surface prior to cell seeding.

If the bubble makes it into the growth area, poor cell viability can result. Bubbles are typically cytotoxic to the cells and will rupture their cell membranes. Moreover, bubbles can interfere with mixing and flow. As such, microfluidic systems are extremely sensitive to even a small bubble introduced into the device at any time during cell culture.

One solution to mitigate bubble-based problems is to integrate microfluidic features to prevent bubbles from entering critical areas of a device. There are, in general, two different approaches: trapping versus debubbling. A bubble trap is a structure integrated into the flow system that halts further progress of a bubble through a device. The trapping approach has the advantage that device operation is maintained while the bubbles are trapped. However, because the bubble trap does not remove bubbles from the system, the bubble trap can completely fill with bubbles. At this point, any additional bubbles are sent through the system and lead to problems. In addition, the trap may not catch all the bubbles in the system.

The alternative to the trap is the debubbling demonstrated by Kang et al. *Lab Chip* 8:176-178 (2008). They actively removed bubbles from the system. This method relies upon the gas permeability of PDMS and uses positive pressure to force bubbles out of the channel and up into the polymer. The advantage here is that the bubbles are removed from the system. However, in order to achieve this, the device has to be sealed, the flow stopped, and the device pressurized to force bubbles out through the polymer. For a microfluidic perfusion system, this means that the media supply to the cells is stopped, altering the environment cells and possibly leading to nutritional deficiencies.

What is needed is a method of removing bubbles from a microfluidic device where the flow is not stopped.

SUMMARY OF THE INVENTION

Methods of removing gas or air bubbles from a microfluidic device are described, including one or more bubbles in a microchannel of a microfluidic device, where the flow is not stopped. Indeed, embodiments of methods are described that combine pressure and flow to remove bubbles from a microfluidic device. Bubbles can be removed even where the device is made of a polymer that is largely gas impermeable, since embodiments of the method do not involve forcing bubbles out through the polymer. In one embodiment, at least a portion of a microchannel is treated to make it hydrophilic (or at least more hydrophilic).

In one embodiment, the present invention contemplates a method of reducing bobble volume, comprising: a) providing a microfluidic device comprising a microchannel, said microchannel comprising a bubble, said bubble having a volume; and b) flowing fluid under pressure through said microchannel under conditions such that said bubble volume is reduced. While gas permeable polymers, in a preferred embodiment said microchannel is made of a polymer that is substantially gas impermeable. It is not intended that the present invention be limited to any particular measurement of gas impermeability; however in one embodiment, it is measured by the rate of oxygen transmission (e.g, oxygen transmission rate properties on the order of less than 0.2 cc/100 in$^2$/day, more preferably less than 0.1 cc/100 in$^2$/day, and still more preferably less than 0.01 cc/100 in$^2$/day).

It is not intended that the present invention be limited to any particular polymer that is substantially gas impermeable. In one embodiment, said polymer is a cyclic olefin polymer.

In one embodiment, said microchannel is in fluidic communication with a first reservoir at a first end of said microchannel, and a second reservoir at a second end of said microchannel.

In one embodiment, said first reservoir comprises fluid under a first pressure and said second reservoir comprises fluid under a second pressure, wherein said first pressure is greater than said second pressure. In one embodiment, said microchannel is in a perfusion manifold (and the reservoirs are in the perfusion manifold). In one embodiment, said perfusion manifold is engaged with and in fluidic communication with a microfluidic chip. In one embodiment, said perfusion manifold comprises a skirt, said skirt comprising a side track engaging said microfluidic chip. In one embodiment, said microfluidic chip comprises one or more ports and said perfusion manifold is in fluidic communication with said microfluidic chip through said one or more ports. In one embodiment, said perfusion manifold delivers fluid to said microfluidic chip at a flow rate through said one or more ports. In one embodiment, said first pressure is 21 kPa and said second pressure is 20 kPa. In one embodiment, said bubble is a gas bubble. In one embodiment, said gas is oxygen, nitrogen or a mixture thereof. In one embodiment, said bubble is an air bubble. In one embodiment, said flow rate is 40 uL/hr. In one embodiment, said flow rate is greater than 40 uL/hr. In one embodiment, said flow rate is 50 uL/hr. In one embodiment, said flow rate is between 50 and 75 uL/hr. In one embodiment, said microfluidic device comprises viable cells in said microchannel and said fluid comprises media supplied to said viable cells (e.g. via a perfusion manifold of the type shown in FIGS. 1A and 1B). In one embodiment, said media prior to step b) was degassed. In one embodiment, said media of step b) is unsaturated. In one embodiment, said media prior to step b) was not degassed. In one embodiment, step b) is performed for at least one 1 hour. In one embodiment, step b) is performed for 2 hours. In one embodiment, the method further comprises c) introducing fluid into said microchannel, wherein said fluid has not been degassed.

In yet another embodiment, the present invention contemplates a method of reducing bubble volume, comprising: a) providing a microfluidic device comprising a microchannel, said microchannel made of a polymer that is substantially gas impermeable, said microchannel comprising a bubble, said bubble having a volume; and b) flowing fluid under pressure through said microchannel under conditions such that said bubble volume is reduced. In one embodiment, step b) is performed for between 1 and 2 hours.

In one embodiment, said microchannel is in fluidic communication with a first reservoir at a first end of said microchannel, and a second reservoir at a second end of said microchannel. In one embodiment, said first reservoir comprises fluid under a first pressure and said second reservoir comprises fluid under a second pressure, wherein said first pressure is greater than said second pressure. In one embodiment, said microchannel is in a perfusion manifold (e.g. containing the reservoirs). In one embodiment, said perfusion manifold is engaged with and in fluidic communication with a microfluidic chip. In one embodiment, said perfusion manifold comprises a skirt, said skirt comprising a side track engaging said microfluidic chip. In one embodiment, said microfluidic chip comprises one or more ports and said perfusion manifold is in fluidic communication with said microfluidic chip through said one or more ports. In one embodiment, said first pressure is 21 kPa and said second pressure is 20 kPa. In one embodiment, said bubble is a gas bubble. In one embodiment, said gas is oxygen, nitrogen or a mixture thereof. In one embodiment, said bubble is an air bubble. In one embodiment, said flowing of fluid is at a flow rate of 40 uL/hr. In one embodiment, said flow rate is greater than 40 uL/hr. In one embodiment, said flow rate is 50 uL/hr. In one embodiment, said flow rate is between 50 and 75 uL/hr. In one embodiment, said microfluidic device comprises viable cells in said microchannel and said fluid comprises media supplied to said viable cells. In one embodiment, said media prior to step b) was degassed. In one embodiment, said media of step b) is unsaturated. In one embodiment, said media prior to step b) was not degassed. In one embodiment, step b is performed for less than one hour. In one embodiment, step b) is performed for at least one hour. In one embodiment, step b) is performed for 2 hours. In one embodiment, the method further comprises c) introducing fluid into said microchannel, wherein said fluid has not been degassed.

In yet another embodiment, the present invention contemplates a method of reducing bubble volume, comprising: a) providing a microfluidic device comprising a microchannel, said microchannel comprises living cells attached thereto; b) flowing fluid at a flow rate through said microchannel over said cells; c) detecting a bubble, said bubble having a volume; and d) reducing said bubble volume with pressure without stopping said flowing of said fluid.

In one embodiment, said microchannel is in fluidic communication with a first reservoir at a first end of said microchannel, and a second reservoir at a second end of said microchannel. In one embodiment, said bubble of step c) is positioned against a polymer that is substantially gas impermeable. In one embodiment, said first reservoir comprises fluid under a first pressure and said second reservoir comprises fluid under a second pressure, wherein said first pressure is greater than said second pressure. In one embodiment, said first pressure is 21 kPa and said second pressure is 20 kPa. In one embodiment, said bubble is a gas bubble. In one embodiment, said gas is oxygen, nitrogen or a mixture thereof. In one embodiment, said bubble is an air bubble. In one embodiment, said flow rate is 40 uL/hr. In one embodiment, said flow rate is greater than 40 uL/hr. In one embodiment, said flow rate is 50 uL/hr. In one embodiment, said flow rate is between 50 and 75 uL/hr. In one embodiment, said fluid comprises culture media supplied to said living cells and said cells are still living after step d). In one embodiment, said media prior to step d) was degassed. In one embodiment, said media of step d) is unsaturated. In one embodiment, said media prior to step d) was not degassed. In one embodiment, step d) is performed for at least one 1 hour. In one embodiment, step d) is performed for 2 hours. In one embodiment, the method further comprises e) introducing fluid into said microchannel, wherein said fluid has not been degassed.

In yet another embodiment, the present invention contemplates a method for establishing a fluidic connection, comprising: a) providing a first substrate comprising a first fluidic port, a second substrate comprising a second fluidic port; b) aligning the first and second sets of fluidic ports; c) contacting the first and second fluidic ports to establish a fluidic connection under conditions such that a bubble forms, said bubble having a volume; and d) flowing fluid under pressure through said first or second port under conditions such that said bubble volume is reduced. In one embodiment, said first substrate comprises a guide mechanism adapted to guide the second substrate. In one embodiment, the method further comprises prior to step b) engaging the second substrate with the guide mechanism. In one embodiment, said aligning of step b) is performed with the guide mechanism. In one embodiment, said guide mechanism comprises a guide track positioned on said first substrate, said guide track configured to engage a portion of said second substrate. In one embodiment, said bubble of step c) is positioned against a polymer that is substantially gas impermeable. In one embodiment, said bubble is a gas bubble. In one embodiment, said gas is oxygen, nitrogen or a mixture thereof. In one embodiment, said bubble is an air bubble. In one embodiment, flowing of fluid is at a flow rate of 30-40 uL/hr. In one embodiment, said flow rate is greater than 40 uL/hr. In one embodiment, said flow rate is 50 uL/hr. In one embodiment, said flow rate is between 50 and 75 uL/hr. In one embodiment, said first substrate comprises a channel in fluidic communication with said port. In one embodiment, said channel is a microchannel. In one embodiment, said first substrate is a perfusion manifold (e.g. of the type shown in FIGS. 1A and 1B). In one embodiment, said second substrate is a microfluidic device. In one embodiment, said perfusion manifold engages said microfluidic device at step c) (e.g. as illustrated in FIGS. 1A, 1B, 2C-D, or FIGS. 2E-1, 2E-2, 2E-3). In one embodiment, said microfluidic device comprises a microchannel, said microchannel comprising living cells, and said fluid comprises media supplied to said cells. In one embodiment, said media prior to step d) was degassed. In one embodiment, said media of step d) is unsaturated. In one embodiment, said media prior to step d) was not degassed. In one embodiment, step d) is performed for at least one 1 hour. In one embodiment, step d) is performed for 2 hours. In one embodiment, the method further comprises e) introducing fluid into said microchannel, wherein said fluid has not been degassed.

In yet another embodiment, the present invention contemplates a method of reducing bubble volume, comprising: a) providing a microfluidic device comprising a microchannel, said microchannel comprises living cells attached thereto; b) flowing fluid at a flow rate through said microchannel over said cells, wherein said fluid was treated prior to said flowing so as to render the fluid unsaturated; c) detecting a bubble, said bubble having a volume; and d) reducing said bubble volume with pressure over a period of time without stopping said flowing of said fluid, wherein living cells are in said microchannel after said period of time. In one embodiment, said microchannel is in fluidic communication with a first reservoir at a first end of said microchannel, and a second reservoir at a second end of said microchannel. In one embodiment, said bubble of step c) is positioned against a polymer that is substantially gas impermeable. In one embodiment, said first reservoir comprises fluid under a first pressure and said second reservoir comprises fluid under a second pressure, wherein said first pressure is greater than said second pressure. In one embodiment, the first pressure is greater by at least 0.5 kPa. In one embodiment, said first pressure is 21 kPa and said second pressure is 20 kPa. In one embodiment, said first pressure is 31 kPa and said second pressure is 30 kPa. In one embodiment, said first pressure is 33 kPa and said second pressure is 32 kPa. In one embodiment, said bubble is a gas bubble. In one embodiment, said gas is oxygen, nitrogen or a mixture thereof. In one embodiment, said bubble is an air bubble. In one embodiment, said flowing of fluid is at a flow rate of 30-40 uL/hr. In one embodiment, said flow rate is greater than 40 uL/hr. In one embodiment, said flow rate is 50 uL/hr. In one embodiment, said flow rate is between 50 and 75 uL/hr.

In yet another embodiment, the present invention contemplates a method of using non-equilibrated culture media, comprising: a) providing i) non-equilibrated culture media, and ii) a microfluidic device comprising a microchannel, said microchannel comprises living cells attached thereto; and b) flowing said non-equilibrated culture media at a flow rate under pressure over a period of time through said microchannel over said cells, without stopping said flowing of said fluid, wherein living cells are in said microchannel after said period of time and no bubbles are visible in said microchannel. In one embodiment, said microchannel is in fluidic communication with a first reservoir at a first end of said microchannel, and a second reservoir at a second end of said microchannel. In one embodiment, said first reservoir comprises fluid under a first pressure and said second reservoir comprises fluid under a second pressure, wherein said first pressure is greater than said second pressure. In one embodiment, the first pressure is greater by at least 0.5 kPa. In one embodiment, said first pressure is greater by less than 2 kPa. In one embodiment, said first pressure is 21 kPa and said second pressure is 20 kPa. In one embodiment, said first pressure is 31 kPa and said second pressure is 30 kPa. In one embodiment, said first pressure is 33 kPa and said second pressure is 32 kPa. In one embodiment, said first pressure is 34 kPa and said second pressure is 33 kPa. In one embodiment, said bubble is a gas bubble. In one embodiment, said gas is oxygen, nitrogen or a mixture thereof. In one embodiment, said bubble is an air bubble. In one embodiment, said flowing of non-equilibrated culture media is at a flow rate of 30-40 uL/hr. In one embodiment, said flow rate is greater than 40 uL/hr. In one embodiment, said flow rate is 50 uL/hr. In one embodiment, said flow rate is between 50 and 75 uL/hr.

In still another embodiment, the present invention contemplates, a method of reducing bubble volume in a microfluidic device with two microchannels, comprising: a) providing a microfluidic device comprising first and second microchannels separated by a deformable membrane, wherein a bubble is in said first or second microchannel or both, said bubble having a volume; and b) flowing fluid under pressure through said first and second microchannels under conditions such that said bubble volume is reduced and said deformable membrane is not deformed (or deformed less than 20%, more preferably less than 10% and most preferably less than 5%). In one embodiment, i) said first microchannel is in fluidic communication with a first reservoir at a first end of said first microchannel, and a second reservoir at a second end of said first microchannel and ii) said second microchannel is in fluidic communication with a third reservoir at a first end of said second microchannel, and a fourth reservoir at a second end of said second microchannel. In one embodiment, i) said first reservoir comprises fluid under a first pressure and said second reservoir comprises fluid under a second pressure, wherein said first pressure is greater than said second pressure and ii) said third reservoir comprises fluid under a first pressure and said fourth reservoir comprises fluid under a second pressure, wherein said first pressure is greater than said second pressure. In one embodiment, said first pressure is 21 kPa and said second pressure is 20 kPa. In one embodiment, said first pressure is 31 kPa and said second pressure is 30 kPa. In one embodiment, said first pressure is 33 kPa and said second pressure is 32 kPa. In one embodiment, said first pressure is 34 kPa and said second pressure is 33 kPa. In one embodiment, said second reservoir and said fourth reservoir share a pressure regulator (in order to maintain equal, or very nearly equal, pressures within the two microchannels).

In preferred embodiments, the present invention contemplates utilizing non-equilibrated and non-degassed culture media with microfluidic devices. In one embodiment, the present invention contemplates equilibrating via the process of degassing (physically removing dissolved gas from solution) media before a first pressure/flow cycle—but using non-equilibrated and non-degassed media when replacing media thereafter, i.e. during long-term culture. That is to say, culture media is equilibrated and/or de-gassed once, e.g. at the beginning of the experiment, and then a pressure/flow treatment is utilized for a period of time. In another preferred embodiment, the present invention contemplates using non-equilibrated and non-degassed media even in a first pressure/flow cycle (albeit with higher pressures) whenever culture media is placed into the perfusion manifold or "pod" reservoir(s). In this embodiment, culture media is not equilibrated (i.e. it is non-equilibrated culture media) and has not gone the physical removal of dissolved gas via degassing.

It has been found empirically that 1) cells (including cells sensitive to shear forces such as motor neurons) are capable of handling elevated flow rates, i.e. flow rates that help to facilitate bubble removal, without loss of viability or inhibition of development (e.g. no inhibition of axon growth), 2) capable of handling multiple pressure/flow cycles at 20 kPa applied pressure and that 3) the use of cold media to refill inlet reservoirs during normal media refresh/addition steps did not cause the formation of bubbles after the initial pressure/flow step to remove system bubbles.

DESCRIPTION OF THE INVENTION

In one embodiment, the present invention contemplates putting a microfluidic device in fluidic communication with another microfluidic device, including but not limited to, putting a microfluidic device in fluidic communication with the perfusion manifold assembly. Unfortunately, putting devices in fluidic communication with each other can result in the formation of bubbles (40), as shown schematically in FIGS. 3A and 3B. These can also be trapped when initially filling a gas/air filled chip with fluid. Air bubbles are particularly challenging in microfluidic geometries because they get pinned to surfaces and are hard to flush away with just fluid flow. They pose additional challenges in cell culture devices because they can damage cells through various means.

Moreover, bubbles may grow. For example, they may grow because of equilibration with 5% $CO_2$ and a humid environment. They may grow because of capillary force from hydrophobic surfaces. On the other hand, they may grow because of an oversaturated media due to a pressure drop within the perfusion disposable ("PD").

As noted above, one approach to removing bubbles is the debubbling demonstrated by Kang et al. *Lab Chip* 8:176-178 (2008). They actively removed bubbles from the system by utilizing the gas permeability of PDMS; positive pressure was used to force bubbles out of the channel and up into the polymer. The advantage here is that the bubbles are removed from the system. However, in order to achieve this, the device has to be sealed, the flow stopped, and the device pressurized to force bubbles out. For a microfluidic perfusion system, this means that the media supply to the cells is stopped, altering the environment cells and possibly leading to nutritional deficiencies.

In addition, the Kang et al. approach relies on the gas permeability PDMS. While PDMS is commonly used in microfluidics, there are good reasons for not using such gas permeable materials, i.e. good reasons for using materials that are substantially not gas permeable in a chip. First, it can be difficult to control the gas content of liquids present in a chip if the surrounding material is gas permeable, as the liquid may gain or lose gas content through the gas permeable material. This can be relevant, for example, where one wants to model hypoxic conditions, e.g. hypoxic conditions present in some portions of the intestinal tract (modeled by the so-called "gut-on-chip.") Second, gas permeability can exacerbate bubbles, as bubble can gain gas through the gas permeable material. Third, gas permeable materials often also possess higher gas-carrying capacity, which can fuel bubbles even in the absence of convective gas transport. Fourth, materials that are permeable to gasses such as oxygen are often also more permeable to water vapor. Accordingly, gas permeability of surrounding material can lead to evaporation from the microfluidic device.

While there are good reasons for not using materials such as PDMS, there is more to consider. Materials that may happen to be substantially gas impermeable can be favored for other reasons. For example, COP (cyclic polyolefin), polycarbonate, acrylic or polystyrene materials may be selected due to their compatibility with injection molding, optical clarity, strength or a variety of other parameters. These materials tend to be substantially gas impermeable (at least at typical thicknesses and in comparison with the gas permeability PDMS), but their selection is based on other factors.

In any event, the use of materials that may happen to be substantially gas impermeable makes the debubbling approach of Kang et al. unworkable. The bubbles will not be driven into the polymer.

Of course, one approach is to make the conditions less likely for generating bubbles. For example, one approach is to make the fluid layer hydrophilic or more hydrophilic. This reduces the chance of trapped bubbles during priming. Moreover, bubbles should want to shrink normally if media is at equilibrium.

But once there are bubbles, the present invention contemplates active reduction and/or removal using a combination of pressure and flow. In one embodiment, two reservoirs are employed. One can then utilize either a push based flow method (FIG. 6) or a pull based flow method (FIG. 7). In the pull based flow method, oversaturated media won't be in the critical areas of system. This requires swapping positive pressure regulators with vacuum regulators.

A preferred method, however, utilizes a pressure differential and flow. As shown in FIG. 8, even small pressure differentials ($P_1$ versus $P_2$) result in good pressure (sufficient to reduce bubbles) without requiring unrealistic flow rates. In this method, going below a certain applied pressure results in very long (impractical) periods of time to reduce the bubble volume. Moreover, utilizing such low pressure makes the system sensitive to small changes and inconsistencies.

This does not mean that very high pressures need to be used. Indeed, above a certain pressure there are only diminishing returns, i.e. it takes about the same amount of time (short period) to reduce the bubble volume.

While it is not intended that the present invention be limited to any particular mechanism, it is believed that a) the bubble shrinks due to equilibration with dissolved gas in the media, b) there is insignificant capillary pressure to cause the bubble to shrink, c) there is insignificant vapor pressure so as to cause the bubble to grow, and d) there is no gas permeation through either the chip or the perfusion disposable. Said another way, where the media passing by the bubble is unsaturated or under-saturated, it has the ability to take in/dissolve gas from the bubble. One can increase the amount or volume of gas that the media can consume (dissolve) by either actively removing the dissolved gas (degassing) or by increasing the fluid pressure. In one embodiment, both of these are done concurrently/simultaneously, with the increased pressure actually increasing the dissolved gas carrying capacity of the media. The greater the applied pressure, the greater the increase in media gas carrying capacity, the bigger/faster a bubble can be crushed. However, there is a practical limit to this.

It has been found that it would be difficult to effectively crush bubbles if the media remained static (did not flow past the bubble). The reason for this is the relatively long and narrow geometry of the microchannels. As the media dissolves the bubble, it comes closer and closer to equilibrium/saturation and cannot dissolve any more gas. There is not enough volume of media in the microchannels to fully dissolve the bubbles at "reasonable" applied pressures (not enough gas carrying capacity). However, by flowing new (fresh), under-saturated media past the bubbles, this new media can continue dissolving the bubbles.

Looked at another way, the small geometry of a microchannel puts a limit on the size of the bubble. The bubble is small because the space in the microchannel is small. Thus, the ability/time to dissolves bubbles is dependent on applied pressure, flow rate, and initial volume of the bubble (the bigger the bubble, the longer it takes to fully dissolve). Using small pressure differentials that generate significant absolute pressure, the bubble comes to equilibration with media very quickly (nearly instantaneously) and completely. In a preferred embodiment, the following conditions are used:

Pressure IN=21 kPa
Pressure OUT=20 kPa
Time bubble CRUSH=2 hrs

These conditions work well in practice (i.e. crushing/dissolving bubbles without killing cells). Under these conditions, one should be able to fully remove all the bubbles in 1 hr, but in an abundance of caution, one can run the bubble crush cycle for 2 hrs.

DESCRIPTION OF THE FIGURES

FIG. 2D shows a side view of one embodiment of a chip carrier (with the chip inside) detachably linked to the perfusion manifold assembly, where the retention mechanism is engaged to prevent movement.

FIG. 3A shows two fluidically primed devices with microchannels that are not yet connected.

FIG. 10 is a chart showing how large, multi-week experiments are performed with many microfluidic devices or "chips," underscoring that the task of refreshing the media (e.g. every other day or at key time points) can be burdensome.

FIG. 11A shows the results for 8 pods and FIG. 11B shows the results for 11 pods (the dotted lines show the 20% deviation from the bottom average and the top average).

FIGS. 12A&B show plots of pressure versus time in order to test for lid failure when higher pressures are used for bubble treatment for thin gaskets (FIG. 12A) or thick gaskets (FIG. 12B). FIG. 12A shows that, as the pressure was raised and approached 25-30 kPa, the perfusion system with a thin gasket exhibited lid failure.

DEFINITIONS

Figure 1A:
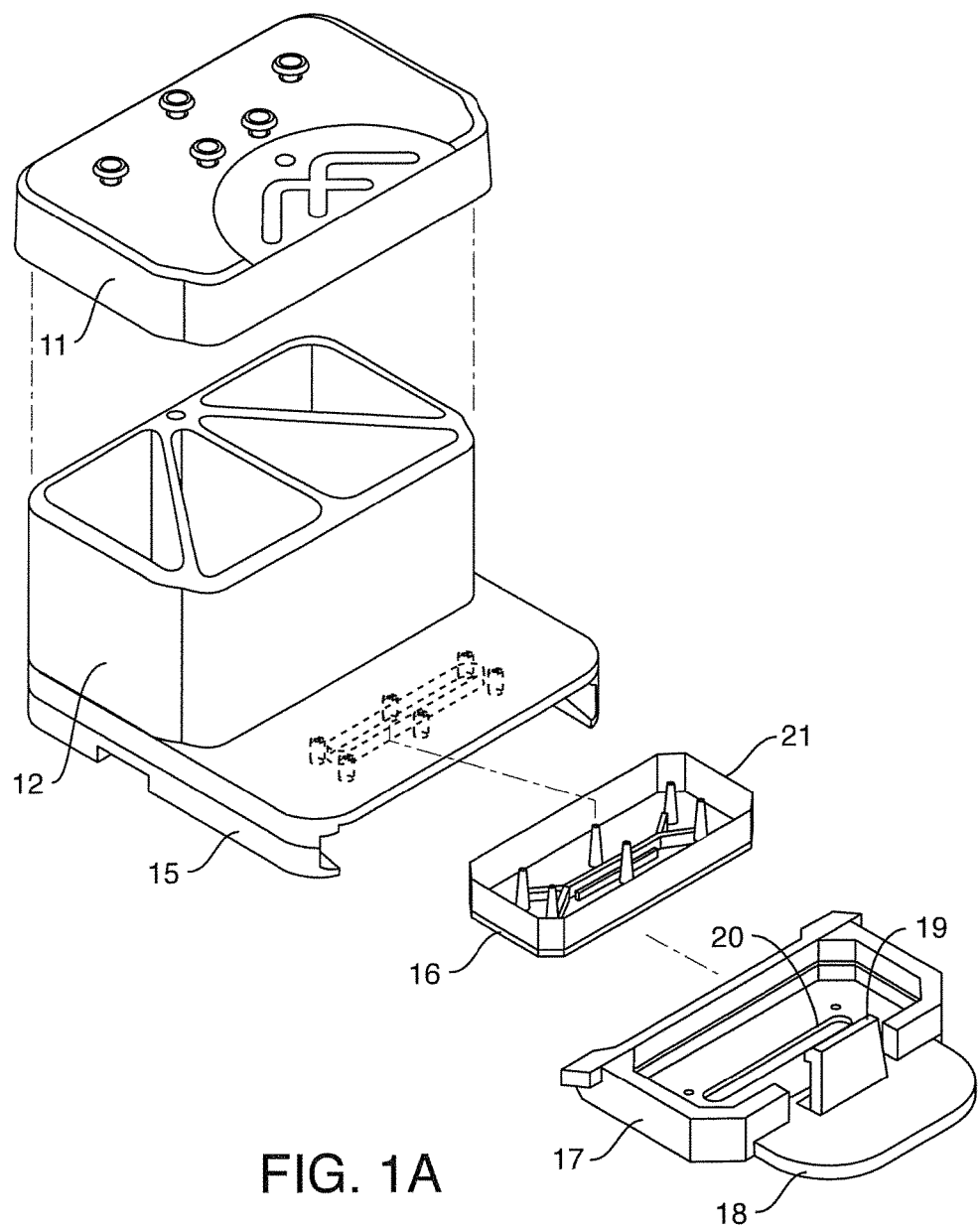
FIG. 1A is an exploded view of one embodiment of the perfusion manifold assembly showing the cover off of the reservoirs, the reservoirs above the backplane, the backplane in fluidic communication with the skirt, the skirt with a side track for engaging a representative microfluidic device or "chip" having one or more inlet, outlet and vacuum ports, the chip shown next to (but not in) one embodiment of a chip carrier, the carrier is configured to support and carrier the chip.

"Channels" are pathways (whether straight, curved, single, multiple, in a network, etc.) through a medium (e.g., silicon, glass, polymer, etc.) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron. It is not intended that the present invention be limited to only certain microchannel geometries. In one embodiment, a four-sided microchannel is contemplated. In another embodiment, the microchannel is circular (in the manner of a tube) with curved walls. In yet another embodiment, combination of circular or straight walls are used.

It is not intended that the present invention be limited by the number or nature of channels in the microfluidic device. In some embodiments, the surface can be a surface of a fluid-flowing conduit or passageway disposed in a solid substrate. In some embodiments, the surface can be a solid surface. For example, in one embodiment, the solid surface can be a wall surface of a fluid channel, e.g., a microfluidic channel. However, the method need not be limited to microchannels, since it will work in any confined space where fluid flows.

Additionally, the term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear or resistance). Microfluidic channels can be formed of various geometries to facilitate a wide range of flow rates through the channels.

A "perfusion manifold assembly" is contemplated that allows for perfusion of a microfluidic device, such as an organ on a chip microfluidic device comprising cells that mimic cells in an organ in the body, that is detachably linked with said assembly so that fluid enters ports of the microfluidic device from a fluid reservoir, without tubing, at a controllable flow rate. In one embodiment (see FIGS. 1A and 1B), the perfusion manifold assembly comprises i) a cover or lid configured to serve as the top of ii) one or more fluid reservoirs, iii) a capping layer under said fluid reservoir(s), iv) a fluidic backplane under, and in fluidic communication with, said fluid reservoir(s), said fluidic backplane comprising a resistor, and v) a skirt (for engaging the microfluidic device). In one embodiment, a combination of pressure and flow reduces bubble volume in a perfusion manifold assembly. In one embodiment, the perfusion manifold assembly is made of a polymer that is less gas permeable than PDMS.

In one embodiment, the perfusion manifold is linked to a microfluidic device (e.g. in fluidic communication therewith). Microfluidic devices (or "chips") containing living cells recreate the physiological tissue-tissue interfaces and permit fluid flow. See U.S. Pat. No. 8,647,861, hereby incorporated by reference. Such devices subject the cells to shear stress. In contrast to static 2D culture, microchannels allow the perfusion of cell culture medium throughout the cell culture during in vitro studies and as such offer a more in vivo-like physical environment. In simple terms, an inlet port allows injection of fluids such as blood, serum, plasma, cell culture medium (and the like) into a microfluidic channel or chamber (with or without cells). In one embodiment, the present invention contemplates a cell-laden microfluidic channel or chamber. An outlet port then permits the exit of remaining fluid as well as harmful metabolic byproducts. In one embodiment, only flow is used with media previously under-saturated.

In some embodiments, a bubble is trapped in a microfluidic device against a polymer that is largely gas impermeable, such as (but not limited to) a COP. Cyclic olefin copolymers (COCs) and cyclic olefin polymers (COPs) are very attractive thermoplastic resins with potential enhanced properties such as outstanding transparency, good heat resistance, low moisture absorption, good chemical resistance, and low double refraction. COCs are obtained through copolymerization of cycloolefin with ethylene or α-olefin, and commercialized under the trade names APEL® by Mitsui and TOPAS® by TOPAS advanced polymers (TAP: formerly Ticona and Hoechst). COPs are prepared via ring-opening metathesis polymerization (ROMP) of cycloolefin followed by hydrogenation, and commercialized under the trade names Zeonex® and Zeonor® by Zeon [25] and Arton® by Japan Synthetic Rubber (JSR).

DESCRIPTION OF PREFERRED EMBODIMENTS

Methods of removing gas or air bubbles from a microfluidic device are described, including one or more bubbles in a microchannel of a microfluidic device. It is not the presence of air, or gas, in the medium which causes the problem. It is the formation of the bubbles from these gases which cause the problem. The question is why and how these bubbles are formed. If the source of bubble formation is established and then removed, only then this problem can be addressed.

One source of the bubble formation may be explained as follows: cells are provided nutrients from culture media maintained at 37° C. However, the culture media used are generally stored at room temperature (or less) which is lower than 37° C. When a medium is transferred out of storage and heated up to 37° C., there is a change in solubility of the dissolved gasses. The decrease in solubility of the gasses at higher temperatures causes the dissolved gasses to come out of the medium in the form of tiny bubbles which tend to stick to surfaces of the microfluidic device housing the cells, including channel surfaces (and, in particular, microdefects in the channel surfaces). While not intending in any way to limit the present invention to any particular mechanism, it is believed that this process of "bubble growth" requires an initial bubble, sometimes referred to as a nucleation point or "seed bubble," for the gas in solution to diffuse into and transition from dissolved gas into non-dissolved gas pockets or bubbles. However, once the medium is equilibrated at 37° C. the formation of the bubbles slows. Therefore, one partial answer to the question of why and how the bubbles are formed is because of a transitory stage during the heating process of the culture media.

Up to now, it has been believed that a simple solution to avoid this problem is to remove the temperature gradient effect, i.e., avoid transferring low temperature medium directly into the microfluidic device. In other words, one should warm the medium to 37° C. outside the microfluidic device and/or give sufficient time for the medium to equilibrate in a vessel or reservoir at 37° C. (with moderate stirring if needed). Of course, this takes time and the culture media needs to be sterile.

While the practice of de-aeration or "de-gassing" has been introduced to address this problem of bubble formation, it is a practice that has practical limitations. The commonly suggested procedure of de-aerating, which is based on heating/vacuum steps, is oftentimes without a measurable endpoint and highly dependent on the equipment being used to perform the procedure. Therefore, the de-aeration step will be unpredictable with a high degree of variability stemming from exact process parameters and equipment used. Additionally, "de-gassing" can have the consequence of removing gasses from solution that are needed to maintain culture, like oxygen (for cellular respiration) and $CO_2$ (for pH buffering). Moreover, no matter how reproducible one tries to be with the de-aeration step, after de-aeration the medium will quickly start equilibrating itself with the atmospheric gasses. Therefore, until this equilibrium is exactly reached, the system will remain unstable and unreliable.

Where large, multi-week experiments are performed with many microfluidic devices or "chips," the task of refreshing the media (e.g. every other day or at key time points) can be burdensome. This is illustrated in FIG. 10 for a 2 week experiment involving organ-on-chips.

Of course, the physiological environment of the cells in a microfluidic device does not require a de-aerated medium. The degassing is only being done to address the bubble problem.

This brings one to the question of whether (and to what extent) non-equilibrated and non-degassed culture media can be employed with microfluidic devices. In one embodiment, the present invention contemplates equilibrating via the process of degassing (physically removing dissolved gas from solution) media before a first pressure/flow cycle—but using non-equilibrated and non-degassed media when replacing media thereafter, i.e. during long-term culture. In another embodiment, the present invention contemplates using non-equilibrated and non-degassed media even in a first pressure/flow cycle (albeit with higher pressures) whenever culture media is placed into the perfusion manifold or "pod" reservoir(s). In one embodiment, the present invention contemplates adding cold/non-equilibrated media into one or more pod reservoirs.

In the first embodiment, culture media is equilibrated and/or de-gassed once, at the beginning of the experiment, and then a pressure/flow treatment is utilized for a period of time. Ideally, the period of time should be short and insensitive to variability (e.g. 1-2 hours), and the treatment conditions should allow for operating without unrealistically high pressures or flow rates. Without intending to limit the invention in any way to a mechanism of action, it is believed that two forces work in concert to shrink bubbles in such a pressure/flow treatment. First, pressure increases the gas carrying capacity of media. Second, flow (e.g. 40 µL/hr) provides fresh (undersaturated) media into which the bubbles dissolve. It has been empirically observed that oversaturated media cannot grow bubbles that do not exist in the first place. Thereafter, culture media would not need to be equilibrated or degassed when replenishing media. Said another way, the single pressure/flow treatment removes the bubbles (or nucleation points/seed bubbles) and the use of oversaturated media thereafter will not bring them back. In this embodiment, non-equilibrated media can be used when refilling inlet reservoirs AFTER a single pressure/flow cycle has successfully eliminated system bubbles. The benefit of this approach is that it solves the bubble problem, while decreasing the number of times culture media must be equilibrated and/or degassed.

In the second embodiment, culture media is not equilibrated (i.e. it is non-equilibrated culture media) and has not gone the physical removal of dissolved gas via degassing. In order for this to work, it has been mathematically determined via physical principals and confirmed experimentally that one can increase the pressure (e.g. by 13 kPa or more) during the pressure/flow cycle (e.g, increase from 20 kPa to 33 kPa or more). While not intending to be limited to any particular mechanism, it is believed that this increased pressure increases non-equilibrated media gas carrying capacity to match equilibrated media gas carrying capacity, making the pressure/flow cycle as effective (theoretically) as with non-equilibrated media. The increased pressure can put a strain on the microfluidic system. However, it has been empirically determined that a thicker gasket for the perfusion manifold is one solution to avoiding leaks associated with the increased pressure. Optionally, increased flow rates (from 50 to 75 µL/hr) can also be used (and provide some benefit in terms of robustness of eliminating bubbles) since it has been empirically found that the cells can tolerate the increased flow. With regard to increased pressure, it appears that the pressure differential between the reservoirs (i.e. the inlet and outlet reservoirs) is more important to the viability of the cells than the actual pressures employed. It has been empirically found that pressure differentials of 2 kPa or less are useful, more preferably 1.5 kPa or less, still more preferably 1.0 kPa or less.

DESCRIPTION OF EXEMPLARY MICROFLUIDIC DEVICES

Figure 1B:
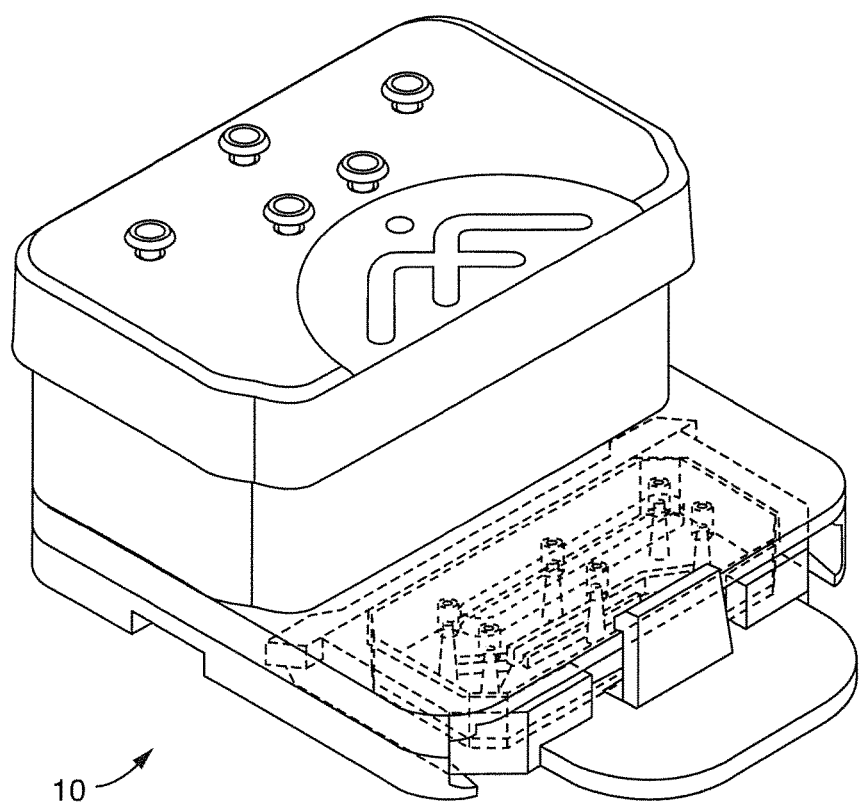
FIG. 1B shows the same embodiment of the perfusion manifold assembly with the cover on and over the reservoirs, and the chip inside the chip carrier fully linked to the skirt of the perfusion manifold assembly, and thereby in fluidic communication with the reservoirs.

In one embodiment (as shown in FIG. 1A), the perfusion manifold assembly or POD (10) comprises i) a cover or lid (11) configured to serve as to top of ii) one or more fluid reservoirs (12), iii) a capping layer (13) under said fluid reservoir(s), iv) a fluidic backplane (14) under, and in fluidic communication with, said fluid reservoir(s), said fluidic backplane comprising a fluidic resistor, and v) a skirt (15) for engaging the microfluidic device (16) which is preferably positioned in a carrier (17). In one embodiment, the carrier (17) has a tab or other gripping platform (18), a retention mechanism such as a clip (19), and a visualization cutout (20) for imaging the chip. In one embodiment, the fluidic resistor comprises a series of switchbacks or serpentine fluid channel (not shown).

Figure 1C:
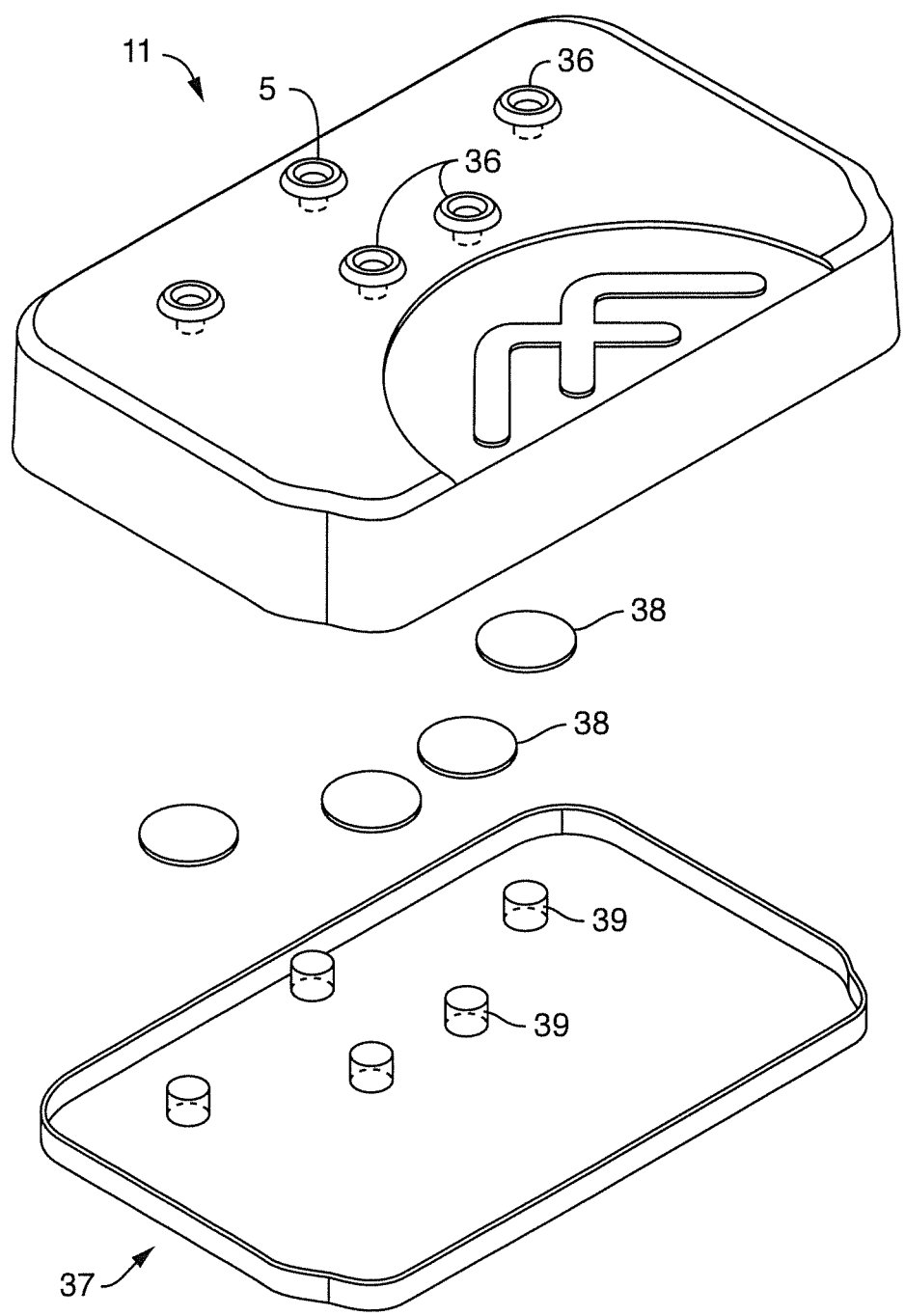
FIG. 1C shows an exploded view of one embodiment of the cover assembly comprising a pressure cover or pressure lid, and an associated gasket thereunder.
Figure 2A:
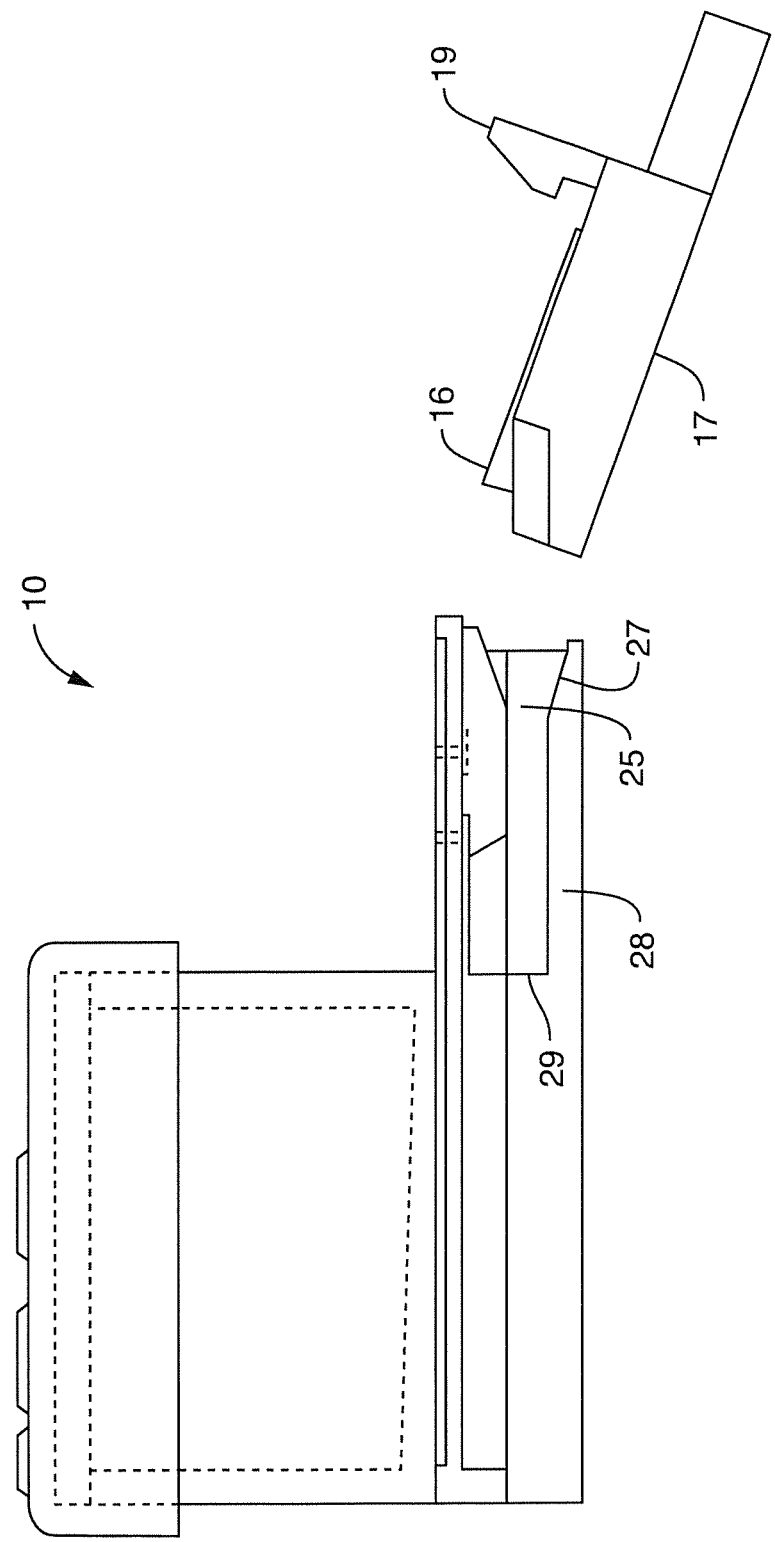
FIG. 2A shows a side view of one embodiment of a chip carrier (with the chip inside) approaching (but not yet engaging) a side track of a skirt of one embodiment of the perfusion manifold assembly, the carrier aligned at an angle matching an angled front end portion of the side track, the carrier comprising a retention mechanism configured as a upwardly protecting clip.
Figure 2B:
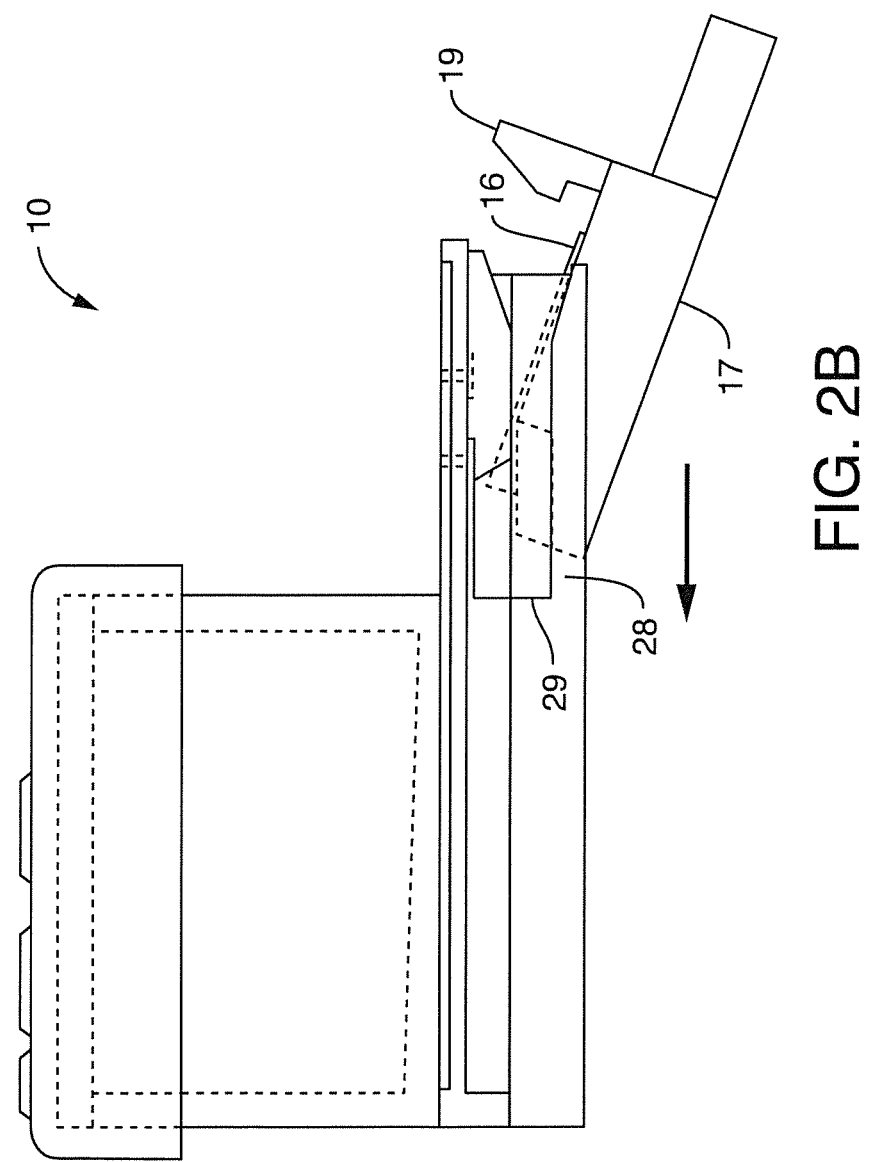
FIG. 2B shows a side view of one embodiment of a chip carrier (with the chip inside) engaging a side track of a skirt of one embodiment of (but not yet linked to) the perfusion manifold assembly.
Figure 2C:
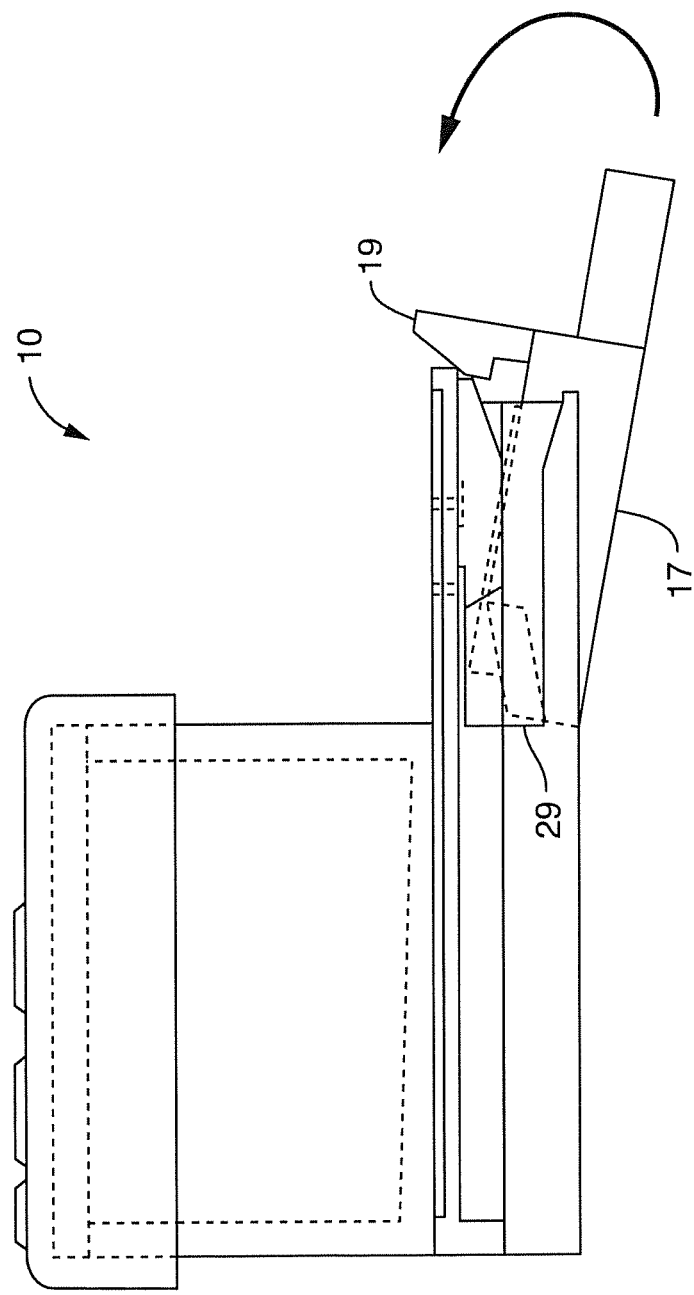
FIG. 2C shows a side view of one embodiment of a chip carrier (with the chip inside) fully engaging a side track of a skirt of one embodiment of (but not yet linked to) the perfusion manifold assembly (with an arrow showing the necessary direction of movement to get a snap fit whereby the retention mechanism will engage to prevent movement).
Figures 1, 2E:
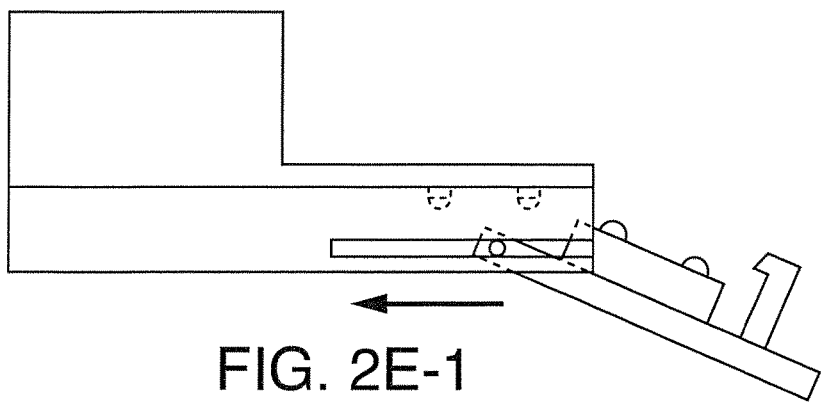
FIG. 2E is a summary slide schematically showing one embodiment of a linking approach to the manifold comprising a sliding action (FIG. 2E-1), pivoting (FIG. 2E-2), and snap fit (FIG. 2E-3) in a single action.
Figures 2, 2E:
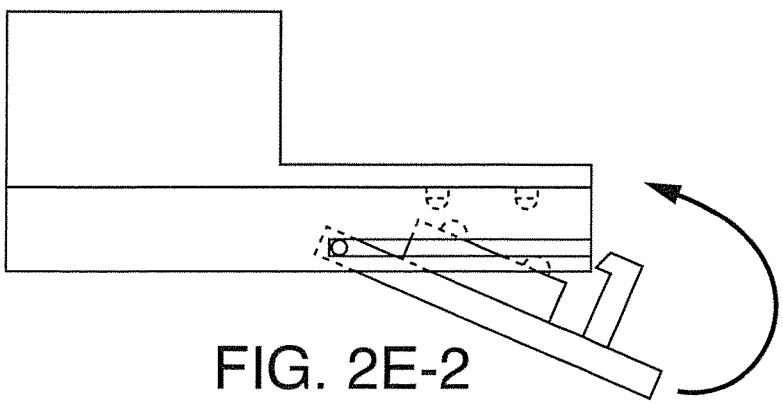
Figures 2, 2E, 3:
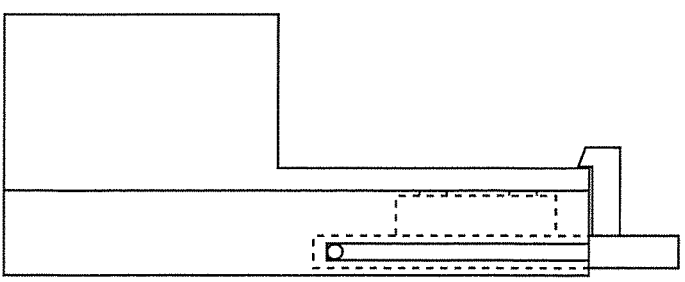
Figure 3A:
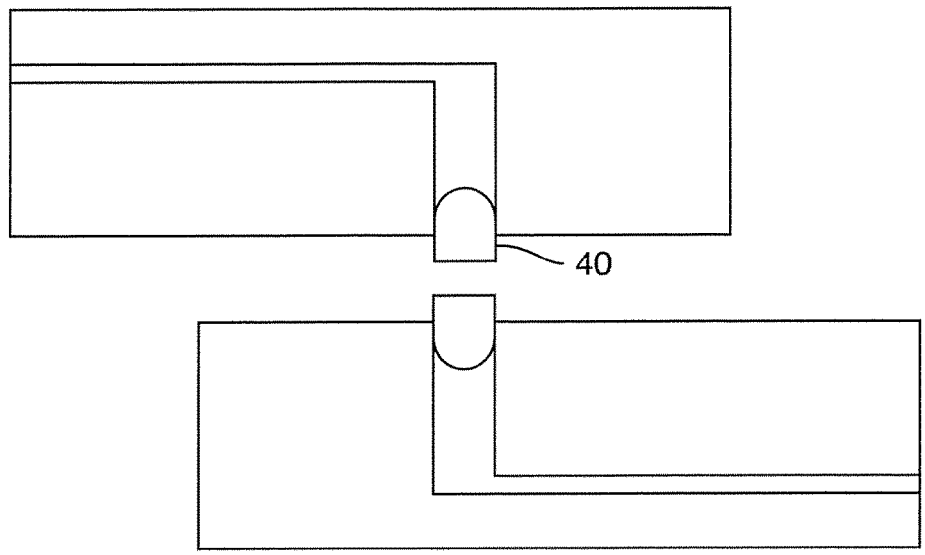
FIGS. 3A&B show schematics showing one embodiment of connecting two microfluidic devices, resulting in the introduction of air or gas bubbles into the microchannels.
Figure 3B:
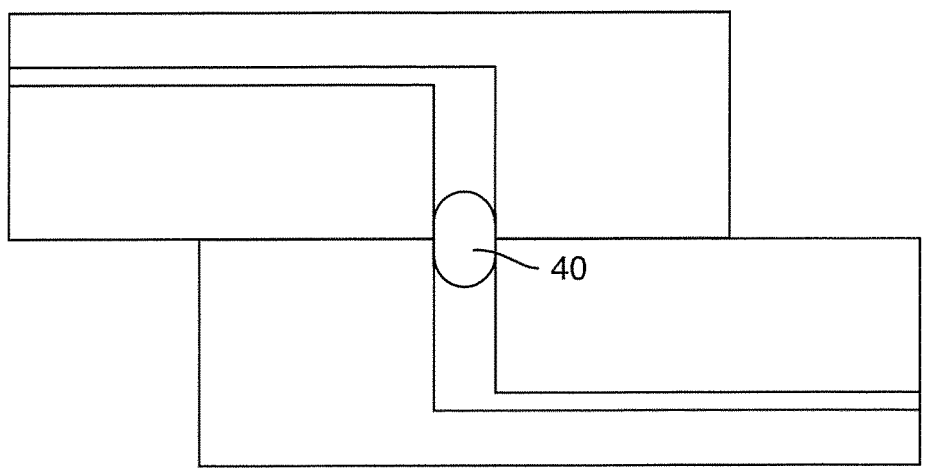
FIG. 3B shows the devices of FIG. 3A contacting in a manner that results in the introduction of air bubbles into the microchannels.

FIG. 1C shows an exploded view of one embodiment of the cover assembly (11) comprising a pressure cover or pressure lid. In the illustrated embodiment, the pressure lid comprises a plurality of ports (e.g. through-hole ports) associated with filters (38) and corresponding holes (39) in a gasket (37). The illustrated design of the holes in the gasket is intended to permit the gasket to aid in retaining the illustrated filters in position. In alternative embodiments, gasket openings may employ a shape different from openings in the lid. For example, the gasket can be shaped to follow the contour of one or more reservoirs with which it is intended to form a fluidic or pressure seal. In some embodiments, a plurality of gaskets may be employed. In a preferred embodiment, a thicker gasket may be employed (in order to avoid leaking under the higher pressures described herein to treat bubbles). In some embodiments, the filters and/or gasket may be fixed using an adhesive, heat stacking, bonding (ultrasonic, solvent-assisted, laser welding), clamped, or captured by elements of the lid and/or an additional substrate. Although the illustrated pressure lid comprises through-hole ports, alternative embodiments comprise one or more channels that route at least one top-surface port to one or more bottom surface ports, which need not be directly underneath the top-surface port.

In one embodiment, the microfluidic device is detachably linked with the manifold assembly by a clipping mechanism that temporarily "locks" the microfluidic device, including organ-on-chip devices, in place (FIGS. 2A, 2B, 2C, 2D and 2E). In one embodiment, the clipping or "snap fitting" involves a projection on the carrier (19) which serves as a retention mechanism when the microfluidic device is positioned. In one embodiment, the clipping mechanism is similar to the interlocking plastic design of a Lego™ chip and comprises a straight-down clip. However, in another embodiment, the clipping mechanism is triggered only after the microfluidic device, or more preferably, the carrier comprising the microfluidic device, engages the perfusion manifold assembly (or cartridge) on a guide rail, side slot, internal or external track (25) or other mechanism that provides a stable glide path for the device as it is conveyed (e.g. by machine or by hand) into position. The guide rail, side slot, internal or external track (25) or other mechanism can be, but need not be, strictly linear and can be positioned in a projecting member or skirt attached to the main body of the manifold assembly. In one embodiment, the beginning portion of the guide rail, side slot, internal or external track or other mechanism comprises an angled slide (27) which provides a larger opening for easier initial positioning, followed by a linear or essentially linear portion (28). In one embodiment, the end portion (29) (close to the corresponding ports of the assembly) of an otherwise linear (or essentially linear) guide rail, side slot, internal track or other mechanism is angled (or curves) upward so that there is a combination of linear movement (e.g. initially) and upward movement to achieve linking.

The POD has a few features that help reduce bubble introduction: 1) the clip has a very smooth engagement—rough engagements and/or jerking motions can introduce bubbles, and 2) the POD diameter going to the chip has been minimized to reduce bubble trapping upon initial filling of the POD—this minimizes dead volume where pockets of air can get trapped.

The advantage of the carrier is that the surfaces of the microfluidic device need not be touched during the detachable linage with the manifold assembly. The carrier can have a plate, platform, handle or other mechanism for gripping the carrier (18), without contacting the mating surface (21) of the microfluidic device (16). The retention mechanism (19) can comprise a projection, hook, latch or lip that engages one or more portions of the manifold assembly, and more preferably the skirt of the manifold assembly, to provide a "snap fit."

Figure 5A:
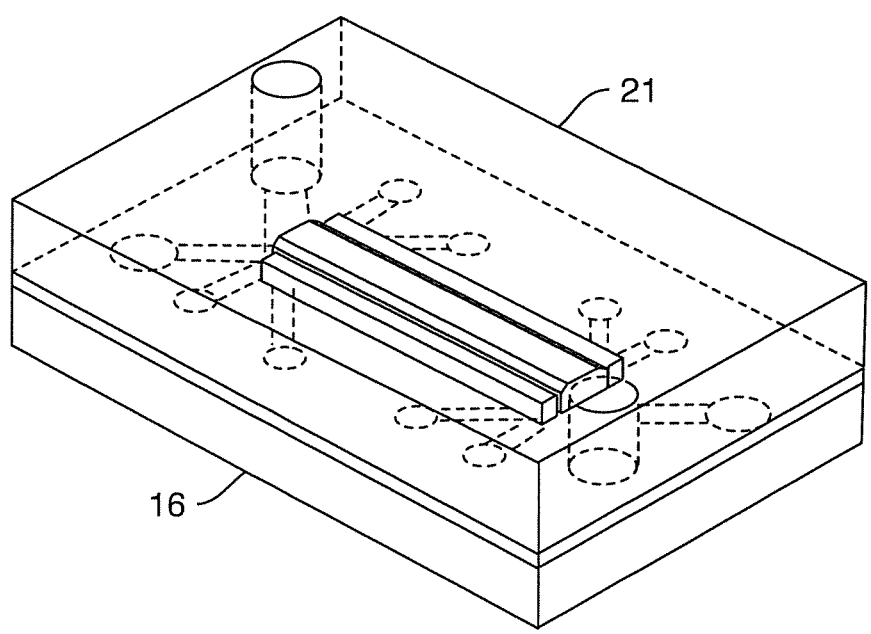
FIG. 5A is a schematic of an illustrative microfluidic device or "organ-on-chip" device (which can be fabricated out of plastic, such as PDMS) with a mating surface (21). The assembled device in FIG. 5A includes a plurality of ports.
Figure 5B:
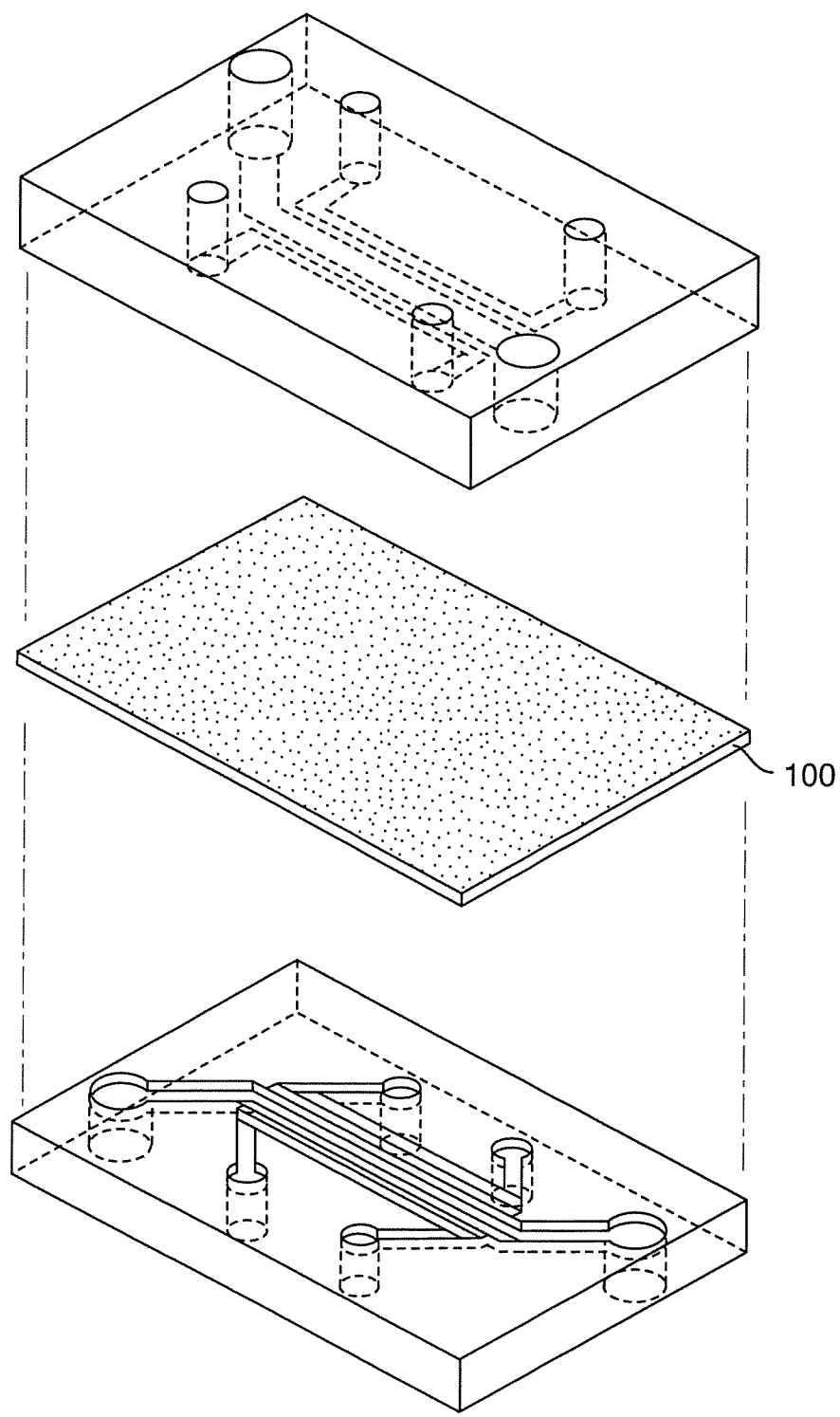
FIG. 5B shows an exploded view of the device of FIG. 5A, showing a tissue-tissue interface simulation region (SR) comprising a membrane, where cell behavior and/or passage of gases, chemicals, molecules, particulates and cells are monitored.
Figure 6:
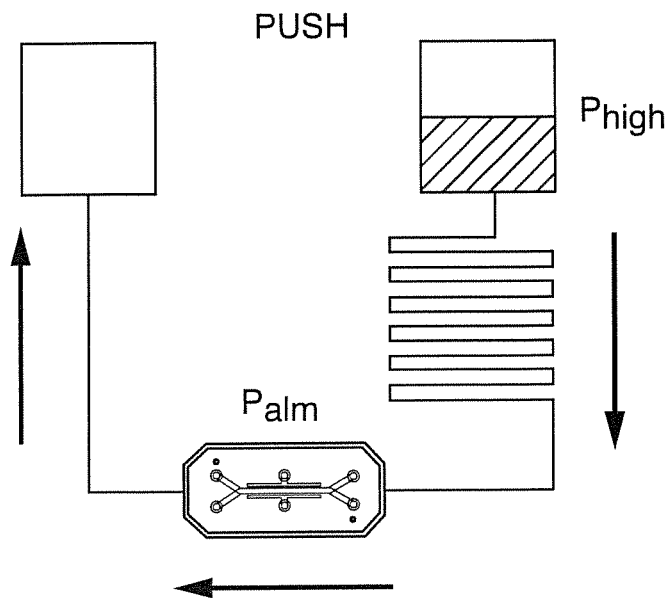
FIG. 6 is a schematic of a "push" based flow approach where fluid flows from a reservoir (on the right) where the fluid is put under high pressure. The fluid exits the reservoir (on the right) and flows in the direction of the chip (see arrows showing the direction of flow) through a resistor (switchback). There is no pressure applied to the other reservoir (on the left)
Figure 7:
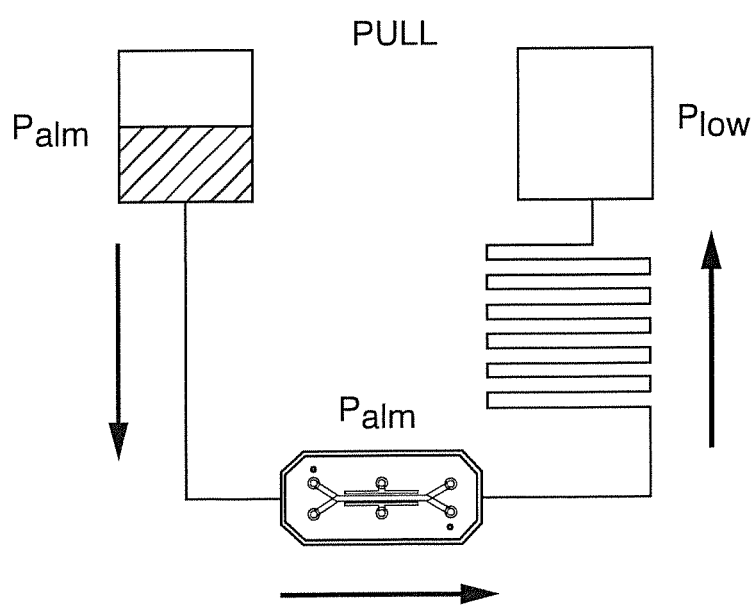
FIG. 7 is a schematic of a "pull" based flow approach where fluid flows from a reservoir (on the left) where the fluid is under no pressure, but where the other reservoir (on the right) has low pressure (e.g. because of a vacuum). The fluid exits the reservoir (on the left) and flows in the direction of the chip (see arrows showing the direction of flow).
Figure 8:
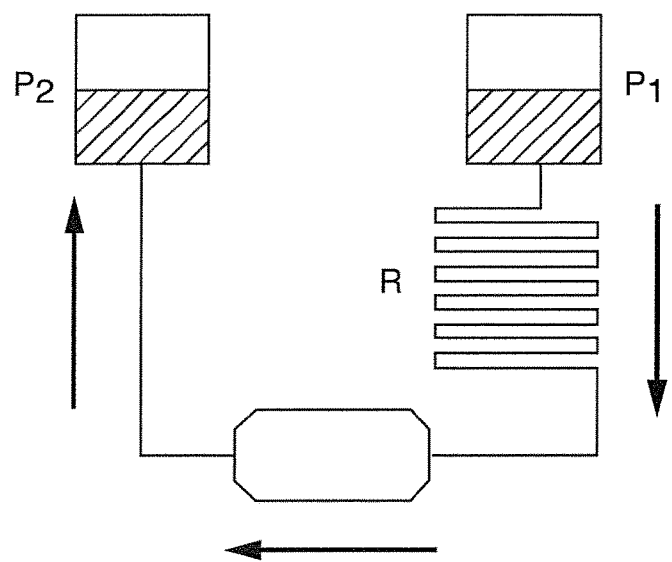
FIG. 8 is a schematic of a pressure differential ("delta P") based flow approach where fluid in both reservoirs are under pressure ($P_2$ is not zero but is less than $P_1$). The fluid exits the reservoir (on the right) and flows in the direction of the chip (see arrows showing the direction of flow) through a resistor (switchback).
Figure 9:
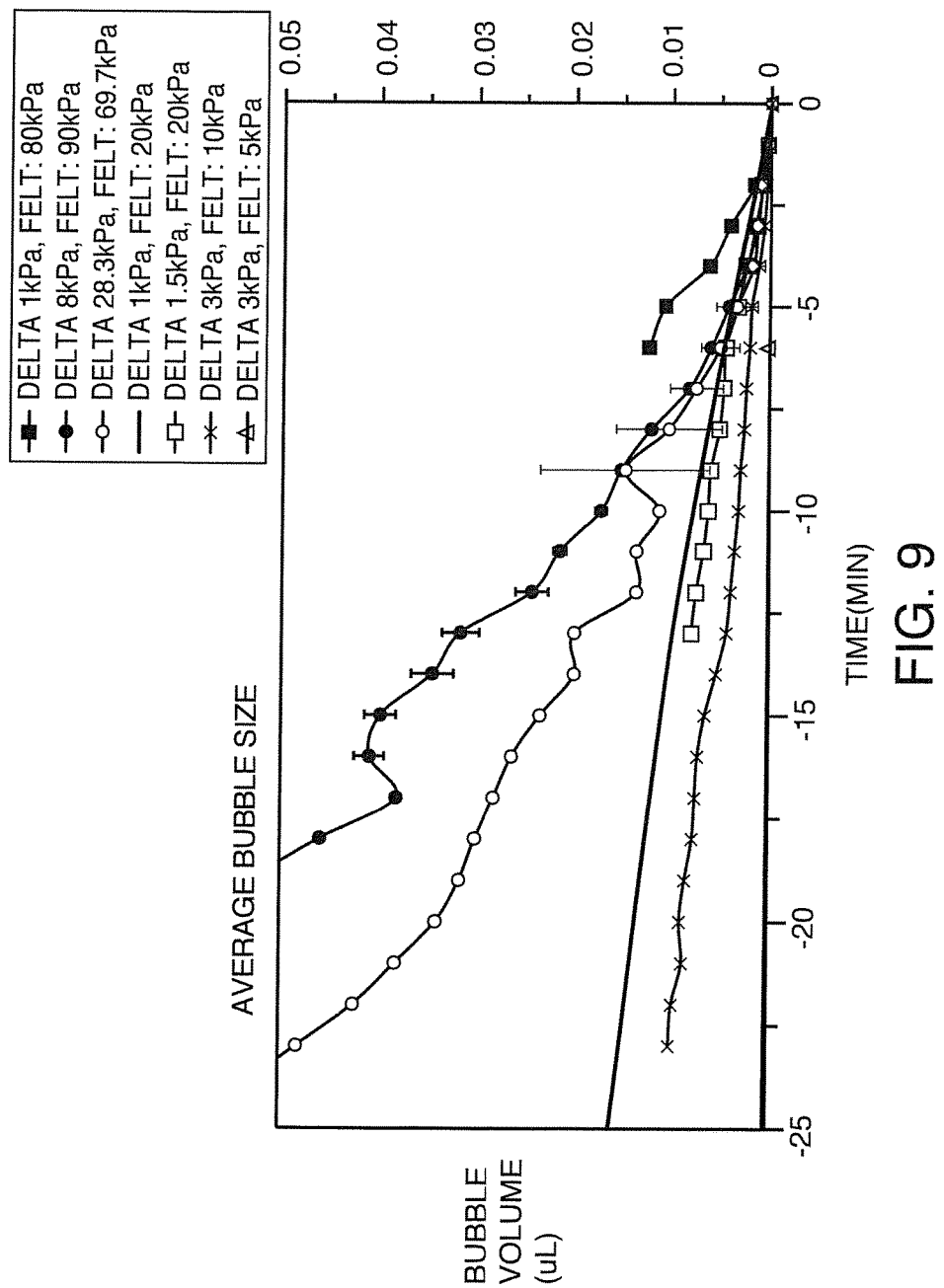
FIG. 9 show experimental results for reducing bubble volume using the pressure differential based flow approach of FIG. 8. The flow rates in FIG. 9 are given in terms of pressure differentials (delta)—1 kPa corresponds to 40 uL/hr, 1.5 kPa is 60 uL/hr, 3 kPa is 120 uL/hr, 8 kPa is 320 uL/hr, 28.3 kPa is 1.13 mL/hr. Pressures applied to the outlets and therefore "felt" by the bubbles are given in terms of "felt" pressure (units of kPa).

FIGS. 5A&B show schematics of illustrative microfluidic devices or "organ-on-chip" devices. The assembled device in FIG. 5A includes a plurality of ports. FIG. 5B shows an exploded view of the device of FIG. 5A, showing a tissue-tissue interface simulation region ("SR") comprising a membrane (100), where cell behavior and/or passage of gases, chemicals, molecules, particulates and cells are monitored.

Figure 4A:
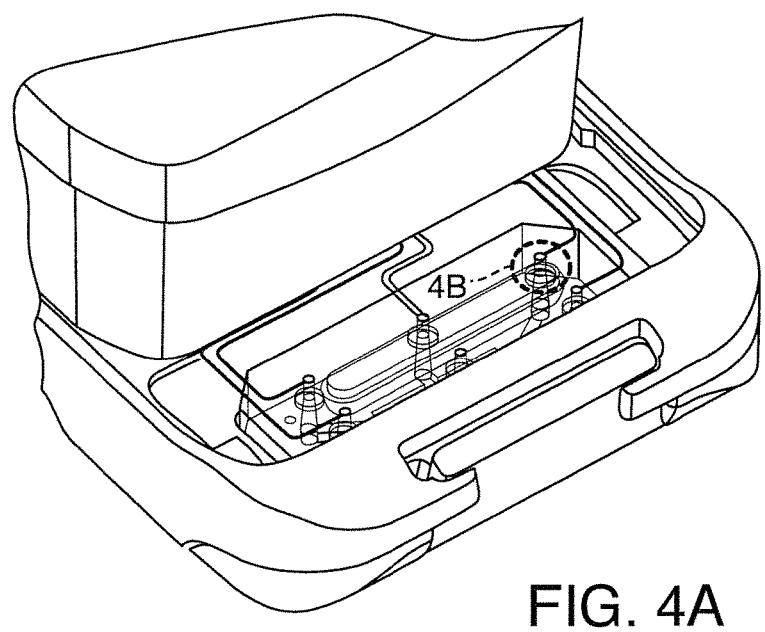
FIG. 4A is a schematic showing the location of a bubble where a chip is engaged by the perfusion manifold assembly (also called the perfusion disposable or POD).
Figure 4B:
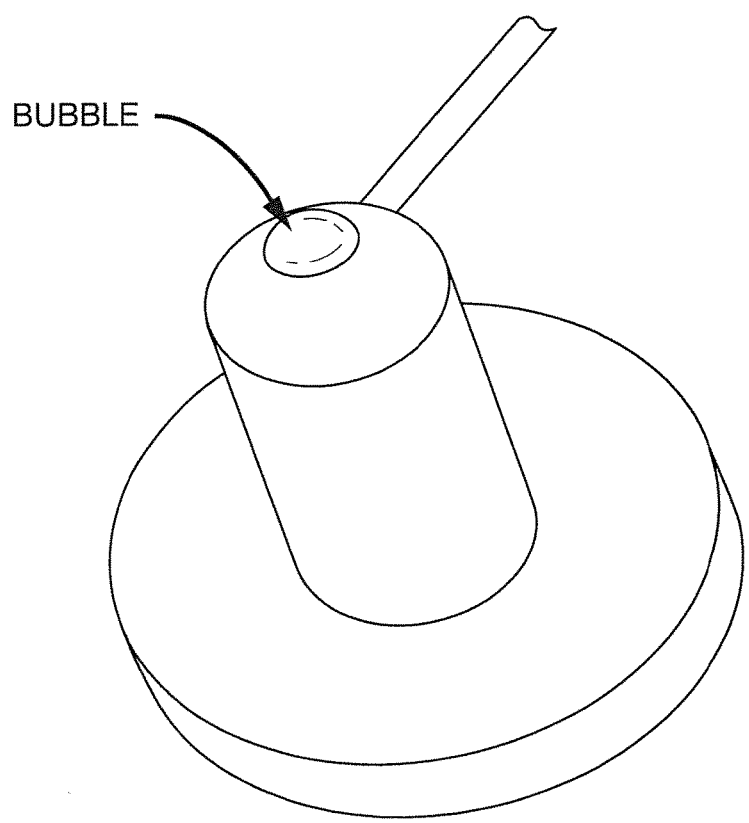
FIG. 4B is a drawing from a photograph of a bubble (see arrow) caught in the perfusion disposable (not the chip) at the location circled in FIG. 4A. The perfusion disposable is comprised of COP (cyclic polyolefin) with a SEBS (Styrene Ethylene Butylene Styrene) capping layer. COP and SEBS are both substantially less gas permeable than PDMS.

Bubbles can be introduced when a chip is engaged by the perfusion manifold assembly (also called the perfusion disposable). FIGS. 4A and 4B underscore this point, showing a bubble (see arrow) caught in the perfusion disposable (not the chip) at the location circled in FIG. 4A. Any one of the embodiments of the methods described above for combining pressure and flow may be used to reduce the volume of such bubbles in such microfluidic devices.

In one embodiment, the POD is positioned on the culture module and the pressure surface of the culture module move down to engage the cover or lid (11) of the perfusion manifold assembly (10). Embodiments of a culture module are described in U.S. patent application Ser. No. 15/248,509, hereby incorporated by reference. As shown in FIG. 1C, the cover or lid comprises ports such as through-hole ports (36) that are engaged by corresponding pressure points on the pressure surface of the culture module. These ports (36), when engaged, transmit applied pressure inward through the cover and through a gasket (37) and apply the pressure to the fluid in the reservoirs (12) of the perfusion manifold assembly (10). Thus, in this embodiment, pressure is applied through the lid (11) and the lid seals against the reservoir(s). For example, when on applies 1 kPa, this nominal pressure results, in one embodiment, in a flow rate of approximately 30-40 uL/hr.

EXPERIMENTAL

Example 1

Figure 11A:
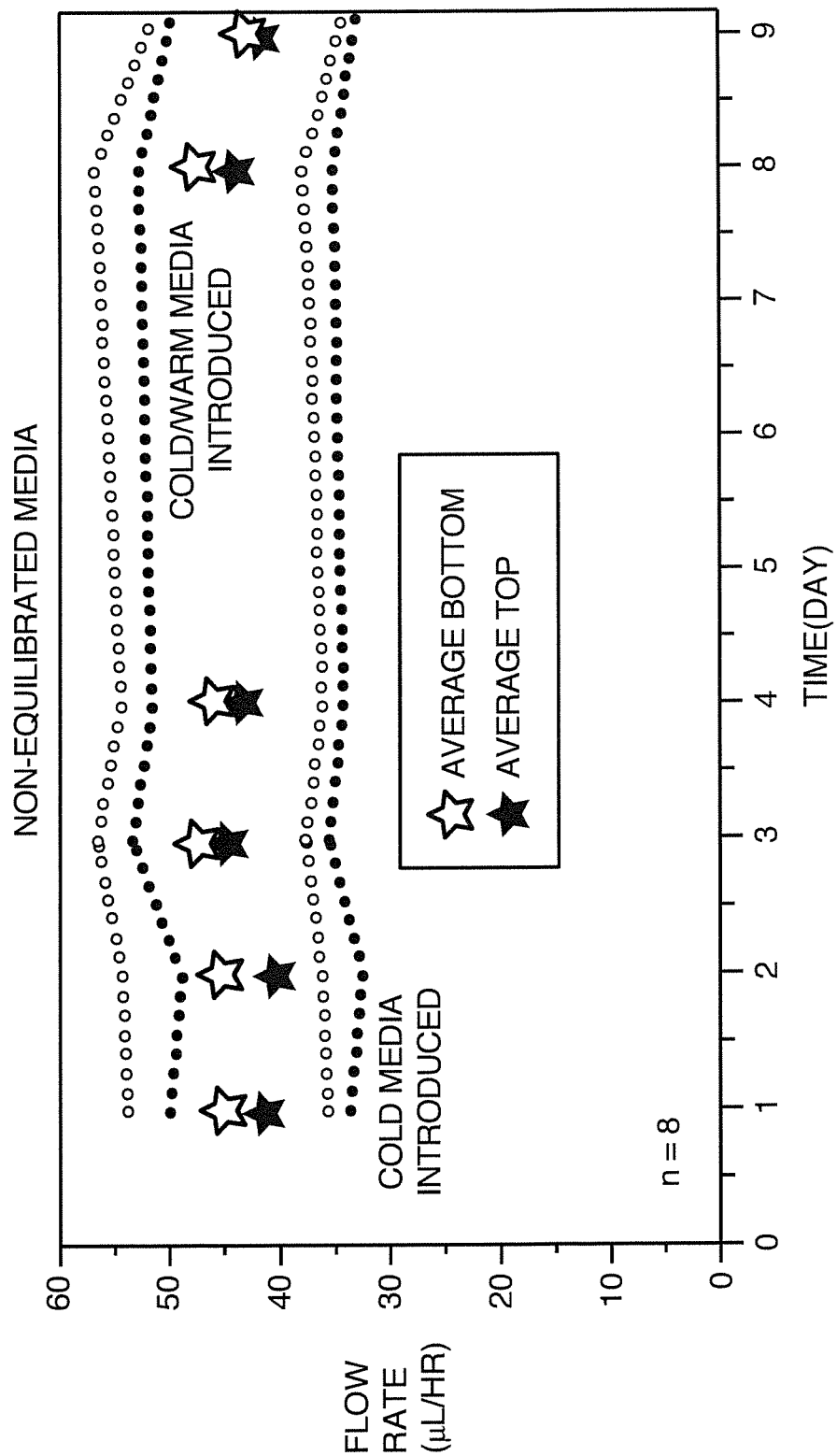
FIGS. 11A&B show the results of an experiment involving the use of non-equilibrated media in 19 pods engaging organs-on-chip, with flow rate as the read-out for detecting bubbles.
Figure 11B:
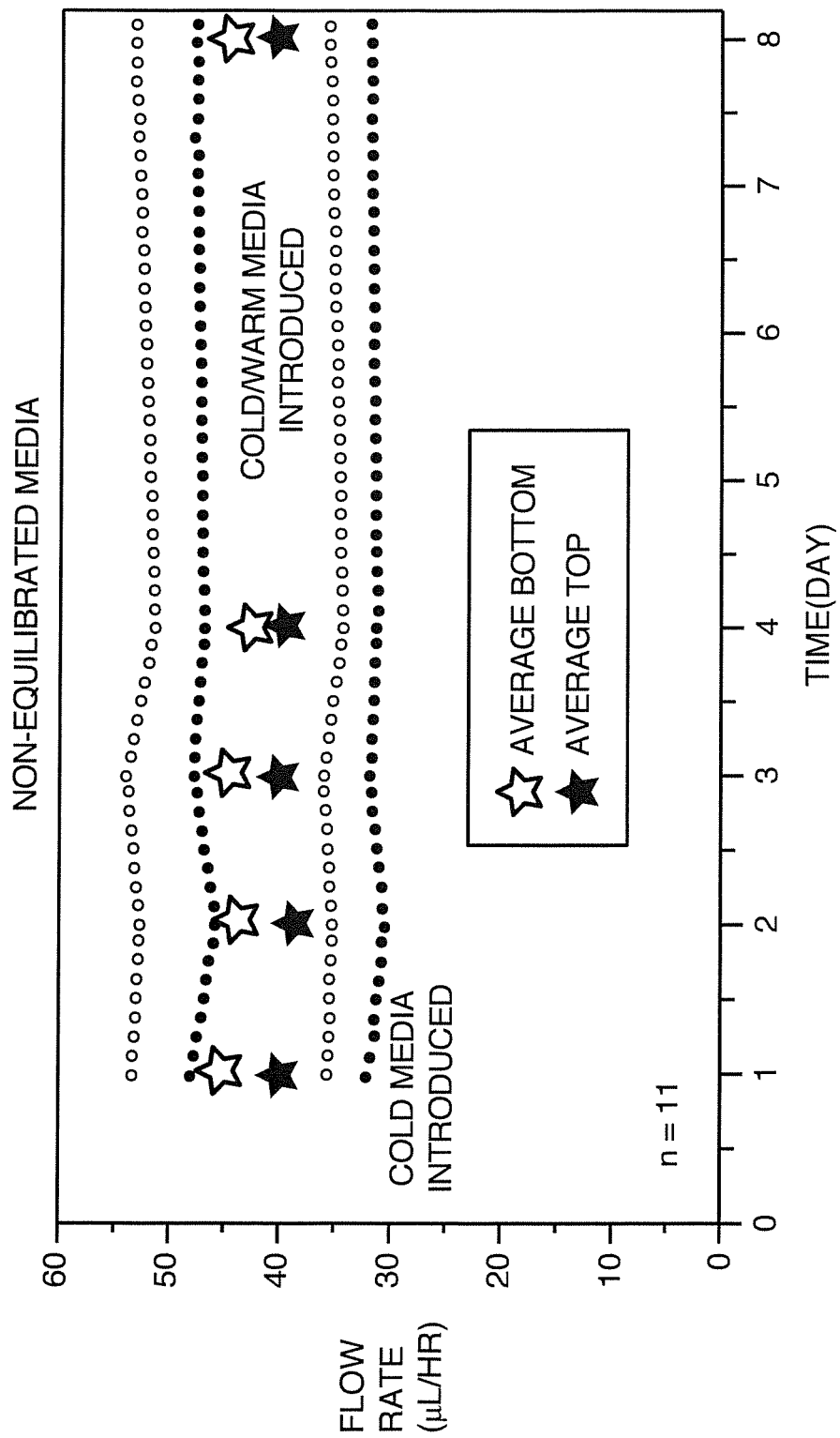

In this experiment, 19 pods engaging organs-on-chip (in this case, microfluidic devices with viable intestinal cells growing on a membrane in a microchannel) were utilized. They were previously running for 6 days, with no history of bubbles. In the test groups, inlet reservoirs were filled with cold media (4° C.) on days 0 and 2, warm media (not equilibrated) on day 7. Flow was measured daily as a read-out (since bubbles disrupt flow and thus a change in flow would indicate bubbles); in addition, the pods/chips were visually inspected for bubbles. The results are shown in FIGS. 11A and 11B. No bubble growth/generation was observed or detected in any pod/chip when using non-equilibrated media (warm or cold) over 9 days.

Example 2

Figure 12B:
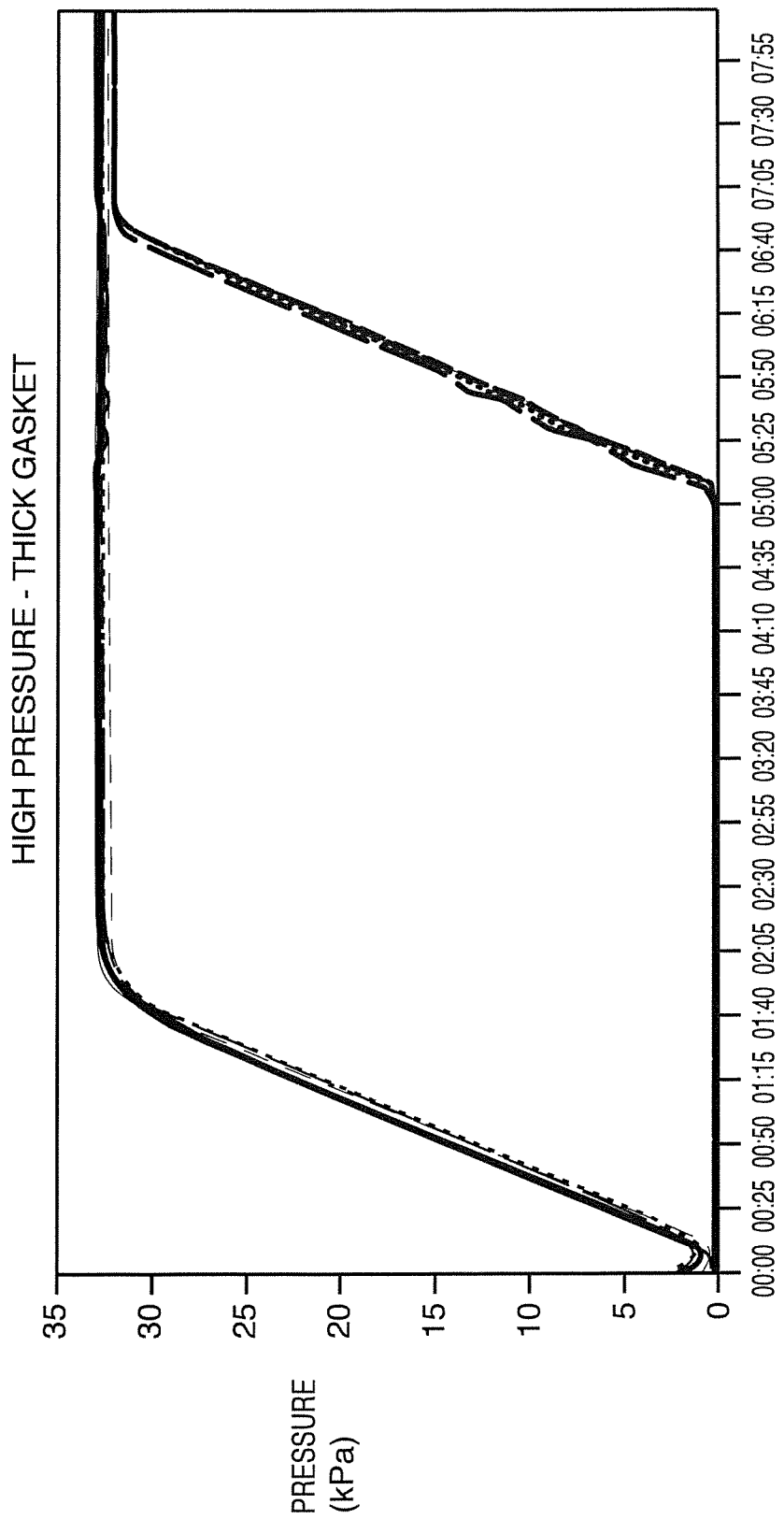
FIG. 12B shows that, as the pressure was raised and approached 33 kPa, the perfusion system with thicker gasket (2-3 times thicker than the thin gasket) did not exhibit lid failure.

In this experiment, one embodiment of the perfusion system's ability to withstand higher pressures was tested (in order to see if working with non-equilibrated media at higher pressures is feasible). Various components on the POD (FIGS. 1A and 1B) were examined, including the lid (FIG. 1C) and other interfaces (e.g. gaskets, bonded components, etc.). In addition, components of a culture module (described in U.S. patent application Ser. No. 15/248,509, hereby incorporated by reference) were examined in these pressure tests (e.g. the manifold, valves and junctions). As the pressure was raised and approached 25-30 kPa, the perfusion system with a thin gasket (FIG. 1C, element 37) exhibited lid failure and leakage (FIG. 12A). However, when a thicker gasket (2-3 times thicker than the thin gasket), there was no lid failure or leakage even at 33 kPa (FIG. 12B). With the thicker gasket, the perfusion system can withstand ~34 kPa on the inlet and ~33 kPa on the outlet.

Example 3

In this experiment, higher flow rates were tested to determine whether there are negative cell effects. More specifically, the viability and function of human primary human motor neurons maintained after 7 days was assessed (since they are relatively sensitive to culture conditions and shear forces). Flow rates of 50 (control) to 75 μL/hr (test) were used to perfuse the cells in a microfluidic chip engaged in a POD (FIGS. 1A and 1B), with the POD engaged with a culture module (described in U.S. patent application Ser. No. 15/248,509, hereby incorporated by reference). The outlet pressure was 20.0 kPa+/−0.5 kPa. The inlet pressure minus the outlet pressure [(Inlet Pressure)−(Outlet Pressure)] was 1.5 kPa+/−0.5 kPa. Primary motor neurons were seeded (on day zero) and cultured for 7 days, and the medium was replenished every two days. A pressure/flow process was run on Days 1 and 5 to treat bubbles. Cold media was placed in the POD reservoir on Days 3 and 5. Cells were imaged (phase contrast captured at 200×).

Figure 13:
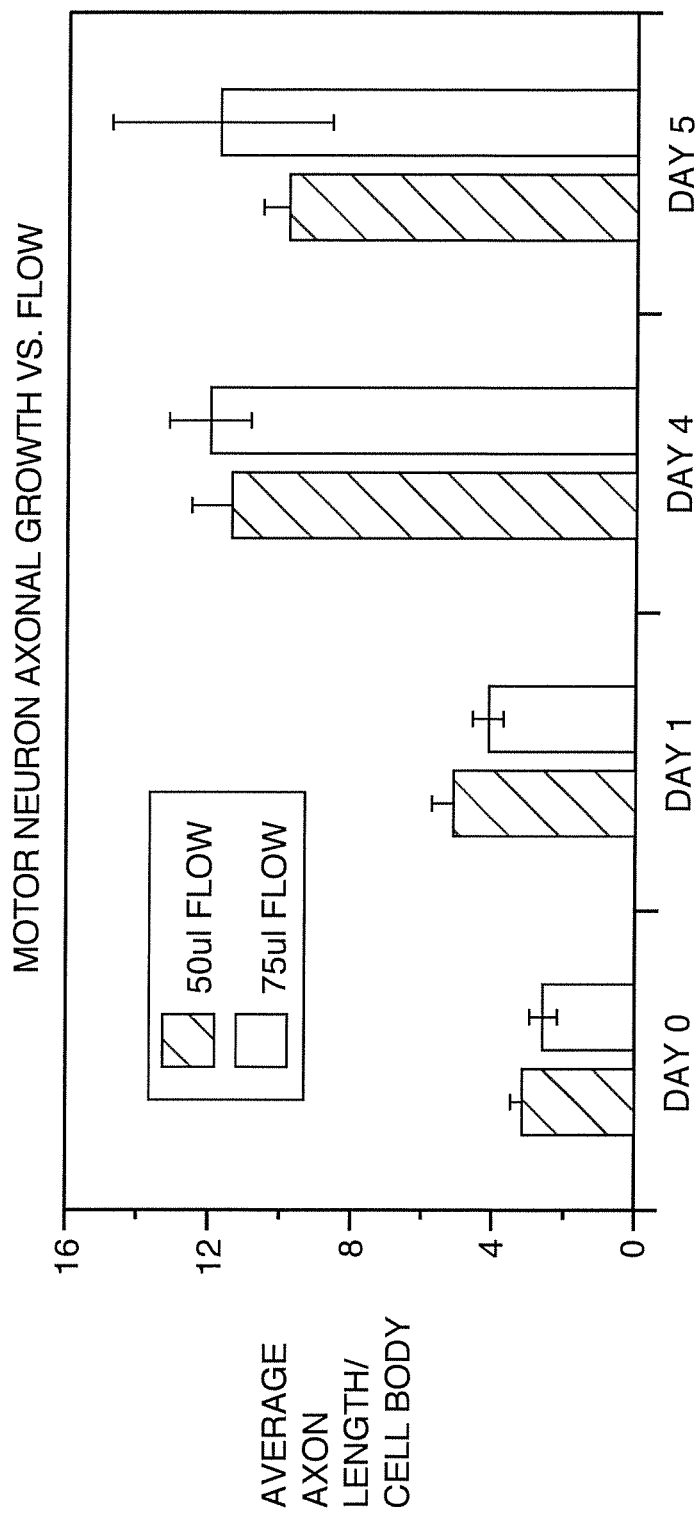
FIG. 13 is a bar graph showing axon growth in a microfluidic device over time (e.g. Day 0, Day 1, Day 4 and Day 5) with 50 µL/hr control conditions versus 75 µL/hr test conditions.

Axon growth was observed in both control and experimental conditions. FIG. 13 is a bar graph showing the results at Day 0, Day 1, Day 4 and Day 5. Results are average±SE in 2 independent PODs for the 50 μL condition and in 3 independent PODs for the 75 μL condition.

Motor neurons were stained (after 7 days) with Hoechst 33342 (blue), which indicates cell nuclei and Tuj-1 (green), which marks β-Tubulin 3—a protein vital to microtubule stability and transport in the axon of neurons. Neuron staining revealed well-developed neuronal networks in the control (50 μL/hr) and in the test (75 μL/hr) (data not shown). In sum, the experiment showed that 1) motor neurons are capable of handling elevated flow rates, i.e. flow rates that help to facilitate bubble removal 2) capable of handling multiple pressure/flow cycles at 20 kPa applied pressure and that 3) the use of cold media to refill inlet reservoirs during normal media refresh/addition steps did not cause the formation of bubbles after the initial pressure/flow step to remove system bubbles.

The invention claimed is:

1. A method of reducing bubble volume, comprising:
   a) providing a microfluidic device comprising a microchannel, said microchannel comprises living cells attached thereto;
   b) flowing fluid at a flow rate through said microchannel over said cells;
   c) detecting a bubble, said bubble having a volume; and
   d) reducing said bubble volume with pressure without stopping said flowing of said fluid.

2. The method of claim 1, wherein said microchannel is in fluidic communication with a first reservoir at a first end of said microchannel, and a second reservoir at a second end of said microchannel.

3. The method of claim 1, wherein said bubble of step c) is positioned against a polymer that is substantially gas impermeable.

4. The method of claim 2, wherein said first reservoir comprises fluid under a first pressure and said second reservoir comprises fluid under a second pressure, wherein said first pressure is greater than said second pressure.

5. The method of claim 4, wherein said first pressure is 21 kPa and said second pressure is 20 kPa.

6. The method of claim 1, wherein said bubble is a gas bubble.

7. The method of claim 6, wherein said gas is oxygen, nitrogen or a mixture thereof.

8. The method of claim 1, wherein said bubble is an air bubble.

9. The method of claim 1, wherein said flow rate is 40 uL/hr.

10. The method of claim 1, wherein said fluid comprises culture media supplied to said living cells and said cells are still living after step d).

11. The method of claim 10, wherein said media prior to step d) was degassed.

12. The method of claim 10, wherein said media of step d) is unsaturated.

13. The method of claim 10, wherein said media prior to step d) was not degassed.

14. The method of claim 1, wherein step d) is performed for at least one 1 hour.

15. The method of claim 14, wherein step d) is performed for 2 hours.

16. The method of claim 14, further comprising e) introducing fluid into said microchannel, wherein said fluid has not been degassed.

17. A method of reducing bubble volume, comprising:
   a) providing a microfluidic device comprising a microchannel, said microchannel comprises living cells attached thereto;
   b) flowing fluid at a flow rate through said microchannel over said cells, wherein said fluid was treated prior to said flowing so as to render the fluid unsaturated;
   c) detecting a bubble, said bubble having a volume; and
   d) reducing said bubble volume with pressure over a period of time without stopping said flowing of said fluid, wherein living cells are in said microchannel after said period of time.

18. The method of claim 17, wherein said microchannel is in fluidic communication with a first reservoir at a first end of said microchannel, and a second reservoir at a second end of said microchannel.

19. The method of claim 17, wherein said bubble of step c) is positioned against a polymer that is substantially gas impermeable.

20. The method of claim 18, wherein said first reservoir comprises fluid under a first pressure and said second reservoir comprises fluid under a second pressure, wherein said first pressure is greater than said second pressure.

21. The method of claim 20, wherein the first pressure is greater by at least 0.5 kPa.

22. The method of claim 20, wherein said first pressure is 21 kPa and said second pressure is 20 kPa.

23. The method of claim 17, wherein said bubble is a gas bubble.

24. The method of claim 23, wherein said gas is oxygen, nitrogen or a mixture thereof.

25. The method of claim 17, wherein said bubble is an air bubble.

26. The method of claim 17, wherein said flowing of fluid is at a flow rate of 40 uL/hr.

* * * * *